US010835650B2

(12) United States Patent
Axon

(10) Patent No.: US 10,835,650 B2
(45) Date of Patent: Nov. 17, 2020

(54) DEVICE FOR COLLECTION OF TISSUE AND METHOD OF USE

(71) Applicant: ARC MEDICAL DESIGN LIMITED, Leeds (GB)

(72) Inventor: Patrick Axon, Leeds (GB)

(73) Assignee: ARC MEDICAL DESIGN LIMITED, Yorkshire (GB)

( * ) Notice: Subject to any disclaimer, the term of this patent is extended or adjusted under 35 U.S.C. 154(b) by 365 days.

(21) Appl. No.: 15/764,486

(22) PCT Filed: Oct. 7, 2016

(86) PCT No.: PCT/GB2016/053131
§ 371 (c)(1),
(2) Date: Mar. 29, 2018

(87) PCT Pub. No.: WO2017/060726
PCT Pub. Date: Apr. 13, 2017

(65) Prior Publication Data
US 2019/0054217 A1 Feb. 21, 2019

(30) Foreign Application Priority Data

Oct. 9, 2015 (GB) .................................. 1517921.1

(51) Int. Cl.
*A61B 5/00* (2006.01)
*A61M 1/00* (2006.01)
(Continued)

(52) U.S. Cl.
CPC ....... *A61M 1/0056* (2013.01); *A61B 10/0283* (2013.01); *A61B 10/04* (2013.01); *A61M 1/0058* (2013.01)

(58) Field of Classification Search
CPC .............. A61M 1/0056; A61M 1/0058; A61B 10/0283; A61B 10/04
See application file for complete search history.

(56) References Cited

U.S. PATENT DOCUMENTS 9,220,485 B2 * 12/2015 Parks ................. A61B 10/0045
2004/0230135 A1 11/2004 Merkle
(Continued)

FOREIGN PATENT DOCUMENTS

EP 1234589 A1 8/2002
WO 2013180952 A1 12/2013

OTHER PUBLICATIONS

International Search Report and Written Opinion issued in corresponding International Patent Application No. PCT/GB2016/053131 dated Jan. 5, 2017 (11 pages).
(Continued)

*Primary Examiner* — Max F Hindenburg
(74) *Attorney, Agent, or Firm* — Kilyk & Bowersox, P.L.L.C.

(57) ABSTRACT

A device for separation and collection of tissue from an effluent stream of tissue and carrier fluid generated in a medical procedure comprises a housing (600) having an upper wall (601*a*), a lower wall (602*a*), a circumferential wall (612) extending between the upper wall and lower wall, an inlet aperture 606*a* for receiving the effluent stream and an outlet aperture (607*a*) for discharge of filtered fluid. The housing encloses a filter member (603*a*) positioned between said upper wall and said lower wall and comprising at least one filter receptacle (615), the upper wall comprising a viewing window (604) for viewing tissue collected in the filter member. The inlet aperture is located beneath the filter member, and the device comprises a fluid pathway (628) for delivering effluent stream received through the inlet aperture into a said filter receptacle from above the filter member. The device can be compact whilst nonetheless allowing visualisation of collected tissue.

30 Claims, 18 Drawing Sheets

(51) Int. Cl.
*A61B 10/02* (2006.01)
*A61B 10/04* (2006.01)

(56) References Cited

U.S. PATENT DOCUMENTS

| | | | | |
|---|---|---|---|---|
| 2006/0271018 | A1* | 11/2006 | Korf | A61M 1/0001 604/541 |
| 2007/0191731 | A1 | 8/2007 | Kaye et al. | |
| 2014/0323914 | A1* | 10/2014 | VanderWoude | A61B 10/02 600/582 |

OTHER PUBLICATIONS

Search Report issued in corresponding UK Patent Application No. GB1517921.1 dated Mar. 10, 2016 (3 pages).
Design U.S. Appl. No. 29/619,878, filed Oct. 3, 2017 (11 pages).
Design U.S. Appl. No. 29/619,879, filed Oct. 3, 2017 (11 pages).

* cited by examiner

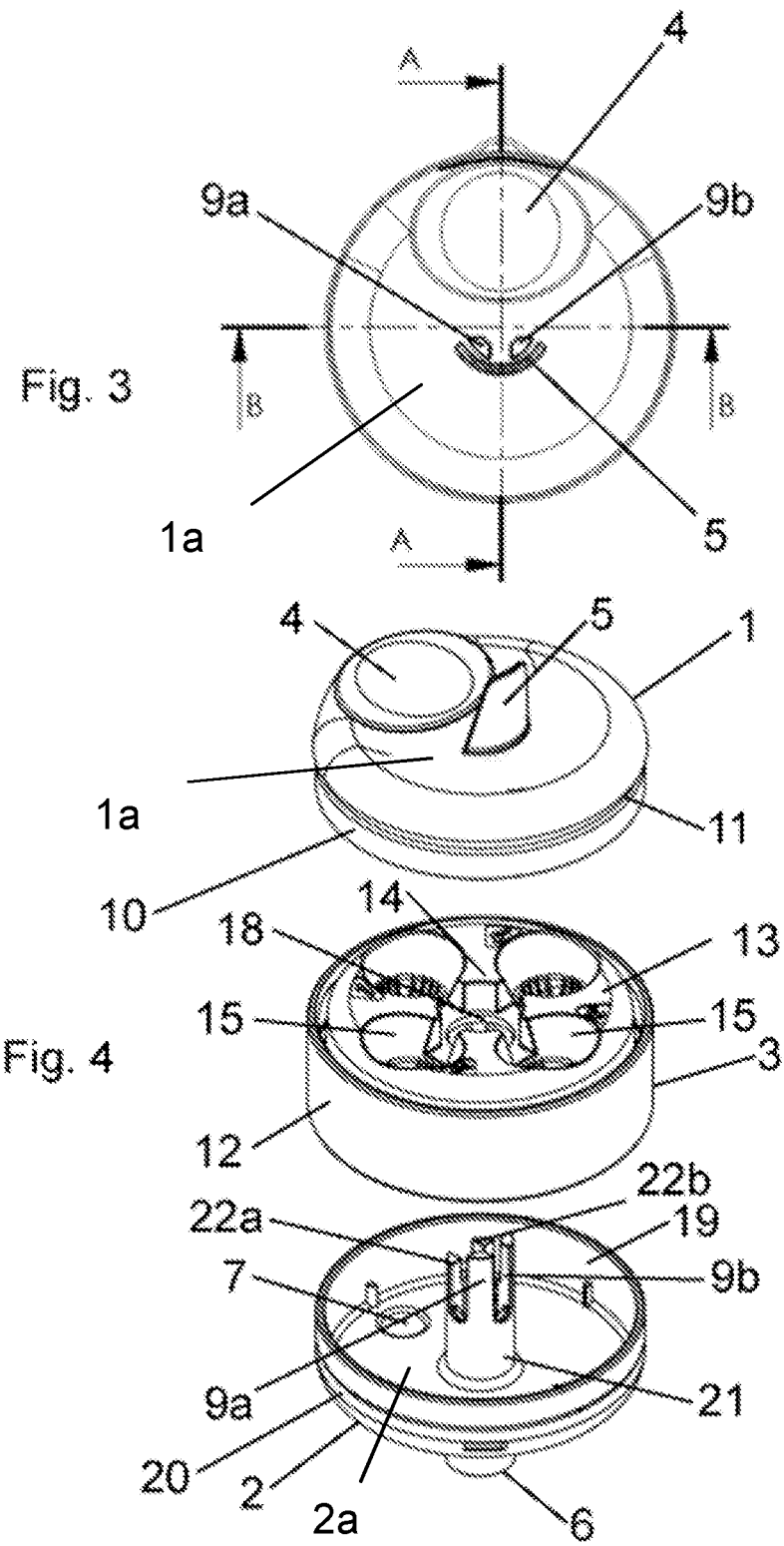

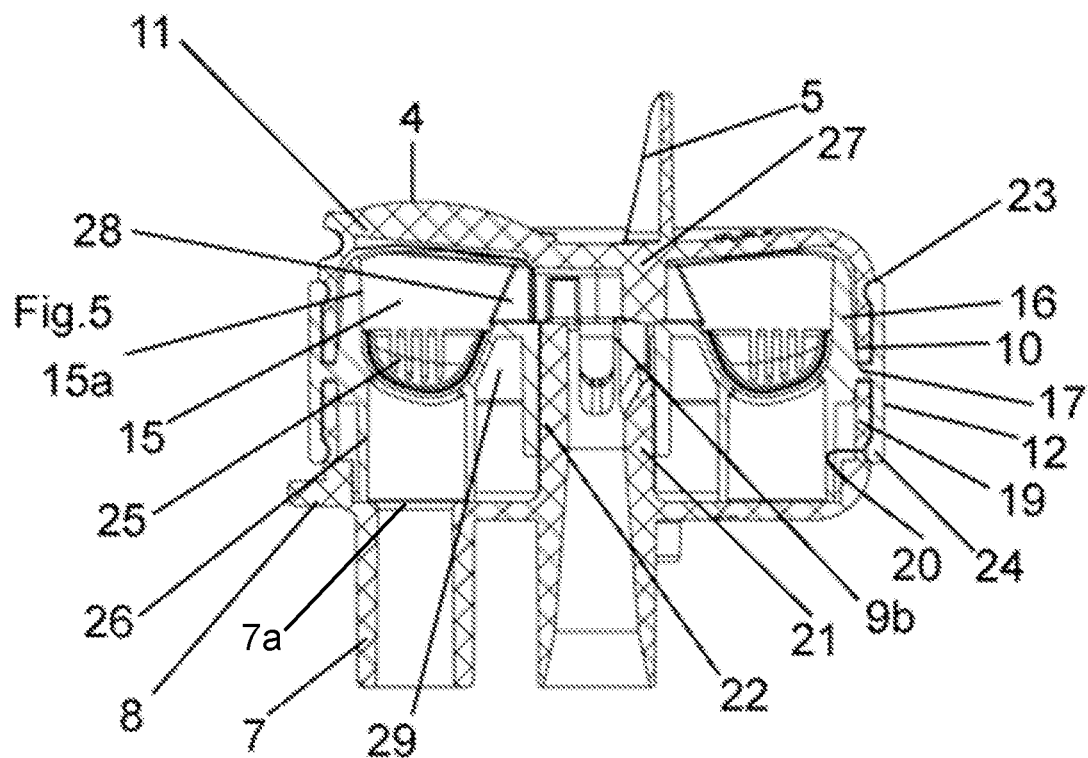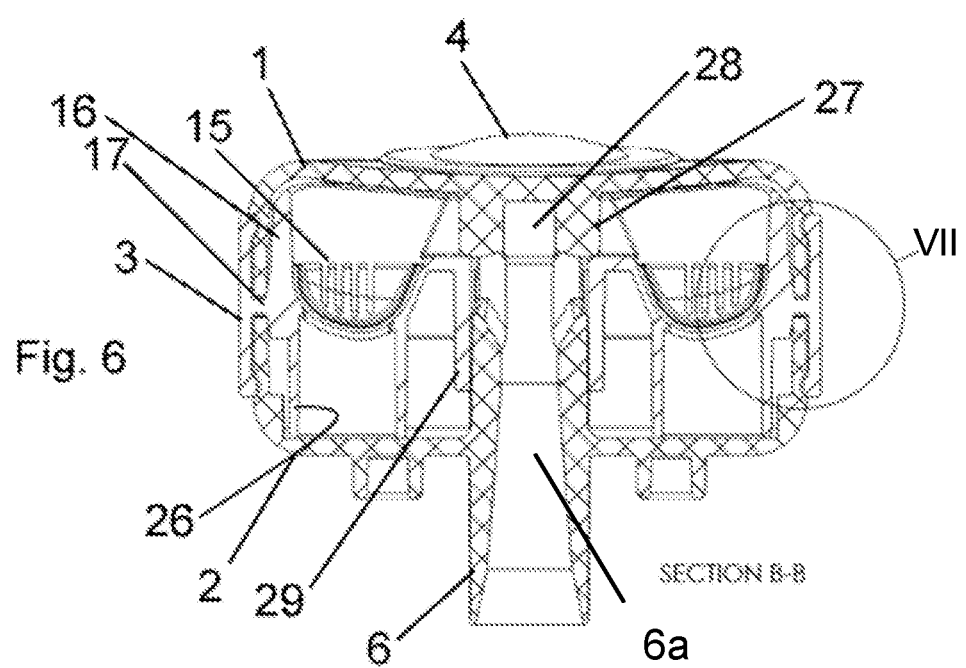

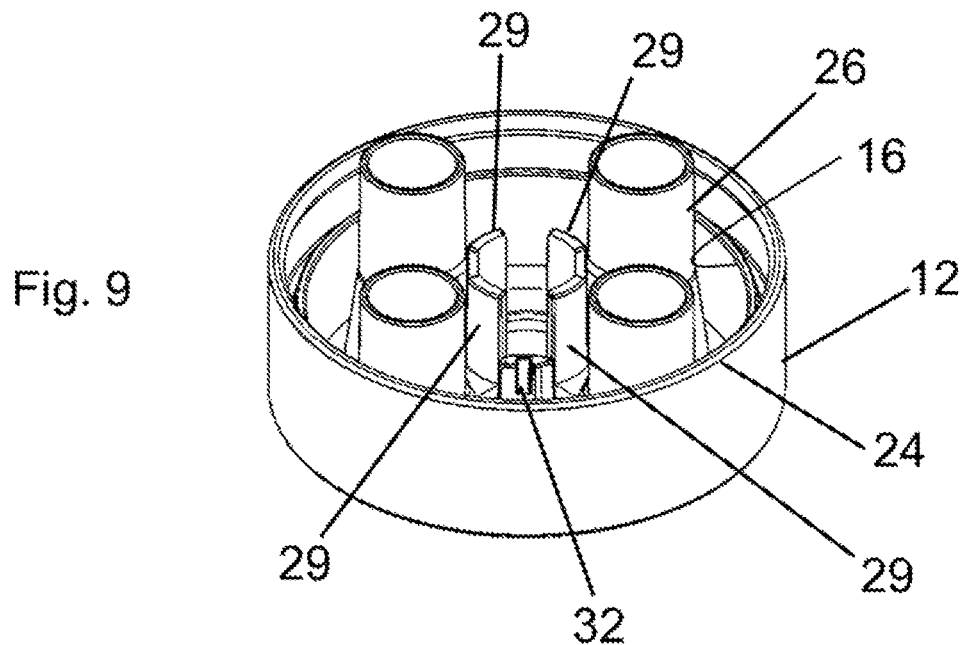
Fig. 9
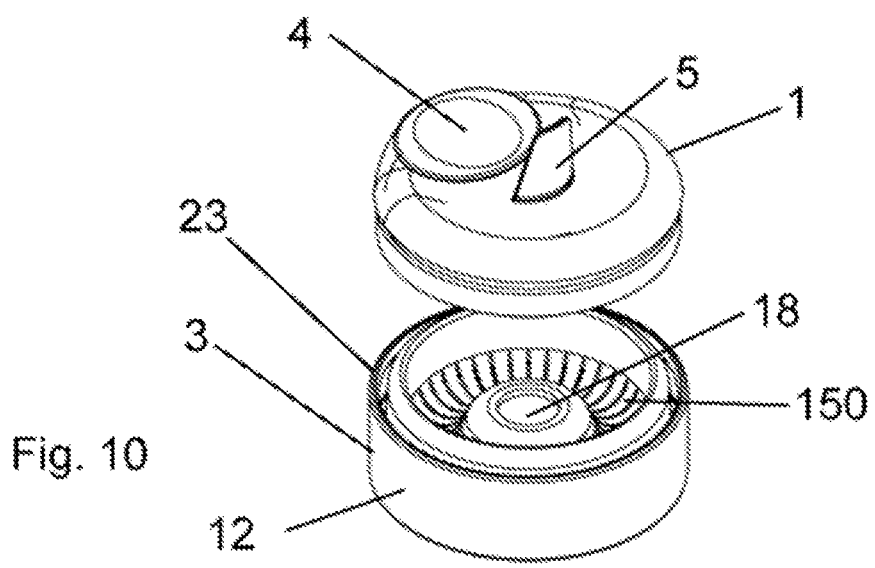
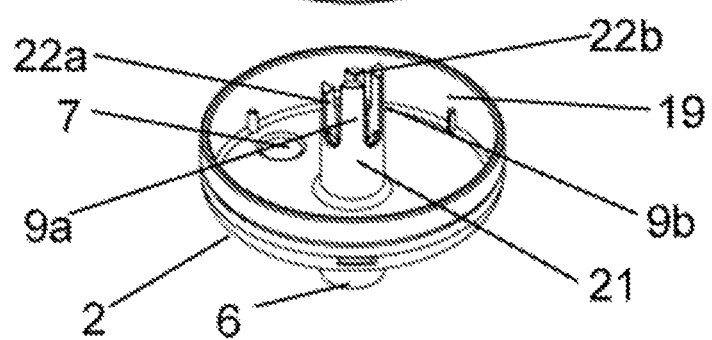
Fig. 10

DEVICE FOR COLLECTION OF TISSUE AND METHOD OF USE

This application is a National Stage Application of PCT/GB2016/053131, filed Oct. 7, 2016, which claims priority to United Kingdom Patent Application No. 1608964.1, filed May 20, 2016, and United Kingdom Patent Application No. 1517921.1, filed Oct. 9, 2015.

The present invention relates to devices for collection of tissue, more particularly to a device for separation from a carrier fluid of tissue collected during a procedure carried out on the human or animal body. The invention also relates to the use of the device, and in particular use of the device for separation of tissue from a fluid flow containing the tissue.

1. BACKGROUND

In internal examination of various body cavities or organs a visualising device is advanced into the cavity or organ. In many examination procedures, the visualising device also includes, or allows for insertion of, a device for removing tissue. By way of example, in endoscopic procedures, flexible instruments designed to view the gastrointestinal tract are inserted along a body cavity to an internal part such as the stomach, duodenum, small intestine or large intestine. The instruments are provided with lighting and imaging devices which enable images to be transmitted and displayed on a television screen. Accordingly, it is possible to view the inside surfaces of the oesophagus, stomach and duodenum using a gastroscope, the small intestine with an enteroscope, part of the colon using a flexible sigmoidoscope and the whole of the large intestine (the bowel) with a colonoscope, enabling anomalies of structure such as polyps or lesions to be identified. Visualisation is in practice generally carried out during slow withdrawal of the instrument, and on sighting of a polyp or lesion a cutting device, for example a snare or blade, may be used to remove tissue from a gastrointestinal surface. In gastrointestinal endoscopic mucosal resection, for example, cancerous or other abnormal lesions are removed from the digestive tract. In other procedures, however, the procedure may be essentially exploratory, with samples being removed for screening purposes. Whether removed merely for screening purposes, because abnormal, or for any other reason, tissue removed in such procedures is often sent for further analysis. Other procedures in which tissue samples are removed for examination include, without limitation, intrauterine procedures to resect and remove tissue including submucous myomas and endometrial polyps, endoscopic mucosal resection of Barrett's oesophagus, and organ biopsies as well as the removal of infected material from body cavities or organs.

In many instruments, a suction system is provided for withdrawal of solids, for example removed tissue or debris, through a conduit within the instrument. On some occasions irrigation fluid is injected and acts as a carrier fluid for flushing the tissue. In practice the effluent stream comprising body fluids and/or irrigation fluid, carrying solid material such as tissue, is withdrawn under suction from the site of the procedure through the conduit and delivered to a fluid transport line outside the patient by means of a source of suction applied via the fluid transport line. A tissue trap may be incorporated into the fluid transport line with the suction source connected to an outlet port of the trap and an inlet port of the trap connected to a suction line from the conduit. In the tissue trap device the tissue can be separated from the carrier fluid for pathological examination. The effluent stream including carrier fluid and entrained solids is typically drawn by the suction source through the trap device, the solids being retained in the trap device and the fluid being removed by suction. The tissue, or a sample thereof, may then be removed from the trap and placed in a sample pot to be sent for pathological examination.

Where one or more tissue samples are collected during a procedure the medical practitioner will generally note the location from which a sample was removed within the organ or cavity since, following pathological examination of the samples, that may provide important information about the location and extent of any disease or abnormality. For the information to be provided by the pathologist to be reliable, it is important that the notes made by the medical practitioner during the procedure are correctly correlated with the samples. Generally tissue samples are removed from a trap at the location of the procedure, for example in an operating theatre, and transferred into sample pots for further pathological analysis. However, errors can arise as a result of inadvertent switching of the samples, with the result that by the time the samples reach the pathology department important notes about the location of collection of the sample are linked with the wrong samples, which may impact on the reliability of the pathologist's conclusions as to the location and extent of a disease or infection.

One known form of trap available commercially has a cup and a round lid, the lid having an eccentrically located inlet port and a centrally located outlet port and forming a friction fit with the open top of the cup to provide a trap that is sealed except for the inlet port and outlet port. The cup contains four basket-shaped filters which are formed integrally with the cup wall in a top region of the cup just underneath the lid. The basket-shaped filters are separated from one another by spaces that extend radially from a central channel defined between the baskets and void regions. The outlet port communicates with an internal tube that extends downwardly through the channel into the bottom of the cup. The lid is so rotatable relative to the cup that the inlet aperture can be located above a selected basket. When suction is applied to the outlet port, an effluent stream drawn into the trap is delivered into the aligned basket, which retains solid material in the stream but allows carrier fluid to pass through the basket into the bottom of the cup, from which it is extracted by suction through the outlet port. After collection of a sample, the lid can be rotated such the inlet is aligned with the next basket, allowing collection of the next solid sample. Optionally, the inlet may be positioned over the intervening void until it is known that there is another sample for collection, thus bypassing the filter baskets when there is no need for collection of material. The baskets may be printed with identifying information, for example numbers, enabling each sample to be indexed with reference to the numbered collection basket, and related to information about the tissue collected, for example the time and location of removal of the tissue. The diameter of the device has to allow for the presence of the intervening void regions. The visibility of the collected samples is poor, and the samples have to be transferred to another receptacle for sending to pathology. In a variant disclosed in US Patent Specification Nos. 2012/053484 and 2014/121560 separable baskets are supported in the container on a grid. The baskets can be used in sequence to collect tissue samples and after completion of sample collection the lid can be removed allowing each basket device and the sample contained therein to be lifted out individually. However, the separate baskets can be difficult to handle and do not address the problems of exposure of operatives to infection and toxic materials and potential transposing of samples.

In another known device described in US Patent Specification No. 8088079, a cuboidal housing has a rectangular upper wall having an inlet port and an outlet port and one side wall is open, permitting insertion of a drawer filter member which seals the housing. The drawer filter member has a basket with multiple apertures in which the sample is collected. The stream carrying the solids is drawn by suction downwards through the inlet port into the drawer where the solids are retained whilst the fluid passes through the apertures into the bottom of the housing where it is drawn upwardly by suction through a conduit to the outlet port. The trap is described as being suitable for collection of multiple samples by means of providing two drawer filter members, which are used alternately. The device is relatively cumbersome, and requires suction to be discontinued during replacement of the drawer member. The sample is removed by hand from the drawer member which potentially exposes the operative to toxic substances or infection, and increases the risk that the sample will be lost or incorrectly labelled.

US Patent Specification 2011106029 discloses a device in which the effluent stream is delivered into a trap from above and passes through a filter with filtered fluid being extracted through a suction discharge passageway in a bottom wall of the trap. Once again, the samples have to be transferred to another container with the associated disadvantages.

It is a common problem in known tissue traps that it can be difficult for the medical operatives (such as attending operating theatre staff) involved in a procedure to gain an unobstructed view within the device to ascertain when a sample has been collected and/or to make a visual assessment of the sample. Frequently, the tubing that communicates with the instrument and/or the tubing that connects the trap to a suction source gets in the way of visualisation of collected tissue. In the case of the relevant procedures, there is generally a significant amount of equipment that is used or must be close at hand, whilst the space for such equipment is limited. It is a disadvantage of known devices in widespread use that the trap has to be opened in order to allow the sample to be removed and placed in formalin pots for sending to pathology which is unhygienic and potentially exposes operators to infection risk. The handling of samples individually by operating theatre staff also raises the risk that samples may be inadvertently swapped so that on reaching pathology they may be associated with the incorrect data regarding collection.

2. SUMMARY OF THE INVENTION

The invention provides, in a first aspect, a device for separation and collection of tissue from an effluent stream of tissue and carrier fluid generated in a medical procedure, the device comprising a housing having an upper wall, a lower wall, a circumferential wall extending between the upper wall and lower wall, an inlet aperture for receiving the effluent stream and an outlet aperture for discharge of filtered fluid, wherein the housing encloses a filter member positioned between said upper wall and said lower wall and comprising at least one filter receptacle, the upper wall comprises a viewing window for viewing tissue collected in the filter member, the inlet aperture is located beneath the filter member, and the device comprises a fluid pathway for delivering effluent stream received through the inlet aperture into a said filter receptacle from above the filter member.

In the device of the invention the effluent stream is admitted to the device in a lower portion of the device, generally in a chamber defined between the filter member and the lower wall. As a result it is possible for the overall size of the device to be relatively small whilst nonetheless allowing good visual inspection of each tissue sample to be achieved without opening the device. It is a further advantage of the invention that the device can be made sufficiently small such that a portion of the device may be placed within standard size preservation containers such as formalin pots without any need to remove a tissue sample or samples from the device. In contrast, it is common practice for tissue samples to be removed from a conventional collection device using a needle or other implement and placed in formalin within a formalin pot, which can lead to biopsy crush damage making pathological inspection difficult. The device of the invention thus has the potential to offer improved hygiene and infection control, with reduced exposure of operatives to toxic or infectious materials and removes the risk of operative needle stick injury that can occur during tissue handling. The device does not need to be opened until it reaches the pathology department where it is to be examined, thereby reducing the direct handling of the tissue samples between collection and pathology examination, which reduces the risks of inadvertent switching of information relating to different tissue samples collected sequentially during a procedure and of damaging the biopsy material before reaching the pathologist.

The invention further provides a method of separating tissue from an effluent stream in which tissue is entrained in a carrier fluid, comprising directing the effluent stream into a device in an upward direction of travel; deflecting at least a part of said effluent stream downwardly into a filter receptacle in which entrained tissue is retained in the filter receptacle and fluid passes through the receptacle, and withdrawing the filtered fluid in a downward direction through an outlet aperture located below the filter receptacle.

References herein to "upper" and "lower" and to "upward" and "downward" relate to orientation of the device in normal use, in which a medical practitioner will normally view the viewing window from above, and do not exclude the possibility that the device may be used in a different orientation. For avoidance of doubt, in practice effluent stream is drawn into the device by suction and the precise direction of travel of the material before and after filtering is not important. The upward and downward directions are thus merely defined with reference to the normal location of the viewing medical practitioner as a matter of mere convenience, that is, the medical practitioner will typically view the device in a downward direction from above.

3. DETAILED DESCRIPTION

In accordance with the invention, an inlet aperture of the device is located in a position beneath the filter member. Preferably it is located in the lower wall of the device, and is especially advantageously located centrally within the lower wall.

The outlet aperture is advantageously located in the lower wall. It is preferred that the inlet aperture is located centrally within the lower wall whilst the outlet aperture is located eccentrically within the lower wall. Central location of the inlet aperture enables it to be in communication with an axially extending fluid pathway within the device as further described with reference to an embodiment below.

Where the inlet aperture and outlet aperture are located away from the viewing window in accordance with the invention, tubing communicating with the inlet and outlet apertures can consequently be easily kept away from the viewing window, reducing the risk that the tubing will get in front of the viewing window and detrimentally affect visualisation of collected tissue therethrough. This advantage is in some embodiments achieved by locating both the inlet aperture and outlet aperture in the lower wall, with any associated structures for connection of the inlet aperture and outlet aperture to tubing for delivery of effluent to and withdrawal of fluid from the housing similarly being associated with the lower wall.

Additionally, as compared with certain conventional traps in which the effluent is delivered into the device from above it is an advantage of the device of the invention that the outlet aperture, when provided at or near the lower wall of the device, can provide for direct removal of fluid from the device after filtering (or without filtering where, in an embodiment described below, there is an optional bypass pathway). In effect, that allows there to be a fluid pathway that extends from the inlet aperture to the outlet aperture without any intervening fluid reservoir. As a result, there is no need to provide a receptacle for the collection of fluid for subsequent removal from the trap. This enables the device to be made smaller and less cumbersome, which inter alia enables it to occupy less space on hospital equipment during use, and to be small enough to be inserted into a standard formalin pot if desired.

Thus, in certain embodiments, the device is so arranged that, in use, substantially all carrier fluid entering the device through the inlet aperture is withdrawn via the outlet aperture. Such embodiments may be reservoir-free, that is, free of any reservoir for collection of carrier fluid. The device of the invention is especially advantageously free from any removable receptacle for collection of carrier fluid.

The filter member may have a single filter receptacle. In some embodiments, however, the filter member comprises at least two, for example from three to five, especially four, filter receptacles.

Advantageously, the filter member is movable, for example rotatable, relative to the rest of the device including the viewing window. Since in some embodiments the inlet aperture is centrally located within the lower wall, the device rotates about the inlet aperture. That is especially advantageous where there is more than one filter receptacle. In one embodiment, where there are multiple, for example four, filter receptacles, distributed around a central axis of the device, the filter member is advantageously so rotatable relative to the rest of the device including the viewing window that a first filter receptacle that lies under the viewing window is rotated to the side until the next filter receptacle is in place under the viewing window. Thus, the filter member can advantageously be rotated under the viewing window to permit each of the multiple filter receptacles to be selectively viewed.

Advantageously the or each filter receptacle comprises a recess having an opening in an upper surface of the filter member and opposed to said upper wall, and a filtration region beneath the opening, the filtration region comprising a fluid-permeable floor comprising apertures for passage of the fluid. The fluid-permeable floor may include any suitable form of aperture provided that the dimensions and configuration of the apertures are such that they will retain tissue samples of the size desired whilst allowing fluid to pass through. Advantageously the filtration region further comprises a drainage region, which advantageously at least in part surrounds the fluid-permeable floor and in which drainage of fluid may occur even when the fluid-permeable floor is occupied by collected tissue. The filtration region is so located and so arranged that in use it will preferentially locate the collected tissue in a region of the filter receptacle that can be readily viewed through the viewing window. The filtration region is advantageously shaped to catch the tissue in the centre of the filtration receptacle enabling ready passage of effluent material around it. The filtration region, and the form of apertures, are designed to enable significant quantities of solid contaminant of the effluent stream in addition to the collected tissue to collect in the filter receptacle without materially reducing flow of effluent fluid around all material.

The apertures in the filtration region may include apertures, which have at least one dimension that is sufficiently small to retain solid tissue samples of a size that it is desired to collect. Typically, the apertures have at least one dimension that is no more than 2 mm, preferably no more than 1 mm. The minimum dimension of the apertures is unimportant provided that, in use, efficient filtering of the effluent fluid can be achieved. Preferably the apertures have a minimum dimension that is no less than 0.5 mm. The apertures may be of any suitable shape, for example, circular, rectangular (including square rectangular), oval. In one advantageous embodiment the fluid-permeable floor comprises a first group of apertures and the filtration region further comprises side regions having further groups of apertures. If desired, any such further groups of apertures may differ in any one or more of size, shape or orientation from the first group of apertures. In certain preferred embodiments the apertures comprise elongate slots. Suitable slots may have a width of, for example, from 0.5 to 2 mm, especially from 0.5 to 1 mm. The length of the slots is greater than, for example at least three or more times the width. In one such embodiment the apertures comprise a first group comprising a plurality, preferably at least three, for example from three to ten elongate slots extending in a first direction and a second group comprising a plurality, preferably at least three, for example from three to ten elongate slots extending in a second direction which is at an angle, for example perpendicular, to the first direction. Furthermore, there may be third or further groups of apertures, each comprising a plurality of apertures, and each comprising for example a plurality of elongate slots. The use of more than one group of apertures, especially for example provided in surfaces that are inclined relative to one another, may be effective in promoting a tendency of collected material to collect in a preferred location, especially a generally central location on the fluid-permeable floor. For example, in a preferred embodiment described below a centre portion of the filtration region may comprise a first group of elongate slots extending along a first direction, whilst at least second and third groups of slots may be arranged at an angle relative to the first group of slots. Advantageously said second, third and optional further groups of apertures, for example slots, are downwardly inclined towards the fluid-permeable floor so as to enhance the tendency of the tissue to collect thereon.

In some embodiments, the device allows selective switching between, on the one hand, a bypass fluid pathway that enables the fluid to pass from the inlet aperture to the outlet aperture without passing through a filter receptacle, and on the other hand, a filter pathway which delivers the fluid to a filter receptacle, or if there is more than one filter receptacle is adjustable to selectively deliver the fluid to each receptacle in turn. In practice, that allows the user to collect a sample in each filter receptacle in turn, for example by rotating the filter member relative to the lower wall so as to direct the fluid in series into each of the filter receptacles until a tissue sample has been collected in that receptacle, whilst if at any point samples are not being collected the user may elect to divert the fluid path to the bypass pathway, which may reduce the amount of unwanted contaminants that will be collected with samples and may also increase the efficiency with which effluent fluid is drawn through the device during periods when tissue is not being collected.

Advantageously, the filter member and the outlet aperture are rotatable relative to one another, whereby the outlet aperture may be aligned with a selected filter receptacle.

Advantageously, the inlet aperture is centrally located within the lower wall and the fluid pathway comprises a through-hole in the filter member, the inlet aperture and the through-hole forming an axially extending pathway communicating between the inlet aperture and an upper chamber defined between the upper wall and the filter member. In a preferred embodiment described herein the fluid pathway comprises an inlet aperture centrally located within the lower wall of the device which communicates with an axially extending channel that permits the incoming effluent stream to be delivered upwardly along an axial path through a central aperture in the filter member and, above the filter member, to be deflected in a radial direction that is selectable. In that way, the effluent stream is directed downwardly through the filter member from above and a particularly compact arrangement is made possible.

In one preferred embodiment, the filter member is mounted within the circumferential wall, and a base member comprising said lower wall and a lid member comprising said upper wall are each removably attached to the circumferential wall. Advantageously, the lid member is attached to the base member, and the lid and base members are rotatable together relative to the filter member.

In practice, it is advantageous for the parts of the device, for example the base member, the lid member and the filter member, when attached together, to fit with enough play such that, on application of suction in use, they are so drawn together that they form a vacuum seal whilst, on ceasing of suction, the seal is released allowing the parts to be disassembled. Furthermore, in practice, it is advantageously possible to remove the base member whilst at least the lid member and filter member remain attached to one another. The attachment should be such that it is relatively easy to remove the lid member when a pathologist wishes to remove the collected tissue for examination.

Advantageously, the device further comprising an indexing and latch mechanism which serves preferentially to position the lower wall selectively in one of a number of filtering positions or in one of a number of positions in which filtering is bypassed. In that manner, reliable delivery of the fluid into the correct location is secured against inadvertent movement. Advantageously, on rotation of the filter member the fluid pathway can be modified so as to deliver effluent stream to the selected filter receptacle. The filter member is advantageously arranged to be rotatable only in one direction so that after using a first filtration receptacle it can only be rotated in a single direction, thereby preventing counter-rotation which could result in inadvertent selection of a receptacle that already contains a previously collected tissue sample.

The viewing member advantageously comprises a magnifying lens, for example a convex lens, so that tissue is magnified for enhanced inspection. The device advantageously includes a measuring scale for permitting measurement of the size of the samples of collected material. For example the viewing member advantageously comprises a magnifying lens including calibrated grid lines, for example on the lens surface, so that it is possible to look through the viewing lens and calculate the diameter of the biopsy material for later recording.

The housing is advantageously substantially sealed with the exception of said inlet aperture and said outlet aperture. However, once collection of samples has been completed, the filter member and lid member may be separable from a base member comprising the inlet and outlet apertures and placed in a preservation container, for example a formalin pot. That enables the formalin (or other tissue preservative substance) to access the filter receptacle through the fluid-permeable floor, thereby enabling the sample to be preserved in formalin in accordance with standard requirements. The device advantageously includes at least one openable air vent which in use is able to permit upward displacement and escape of air by liquid when the device is immersed in liquid, thereby enabling suitable ingress of formalin preservative in which the device may be immersed. Where one or more such air vents are present the device preferably further comprises an obstruction member or members for sealing said air vent or vents during sample collection. On removal of the obstruction member or members, the air vents can thus be opened and on immersion of the device with the air vents into a liquid, for example formalin, the liquid can fill the device thus serving to exclude air, eliminating entrapment of air and allowing preservation of the tissue for later examination. In one embodiment of the invention, air escape apertures provided in the lid member are sealed during normal device use by projections from the base member so that air cannot flow into the device during tissue collection. In that embodiment, the apertures are caused to become open when the base member is detached from the filter member and the lid member.

Advantageously the device has an overall diameter of from 2.5 to 5 cm, for example, 3 to 4.5 cm. That enables the filter member and lid to be placed in a standard 20 ml formalin pot. Placing of the entire filter member, preferably closed by the lid, into a formalin pot enables the samples to be delivered to a pathology department without any need to transfer the samples into a separate container with the risk of associated errors and exposure to toxic or infectious materials. The design of the filter and viewing member is advantageously such that once detached from the base member, the tops of the individual filter receptacles are sealed so that there is no possibility of movement of the biopsy material from one filter receptacle to another or from one filter receptacle into the formalin pot itself.

Advantageously, the device comprises a label. There may be more than one label, particularly where there is more than one receptacle, for example one label relating to each receptacle. The label or labels may be used to carry identifying information for the or each sample, which may include a simple digit or letter uniquely distinguishing each receptacle from the others. It may be possible for the or each label to be used to hold information with regard to a sample, for example, one of more of the date, location from which the sample was taken, by whom, and one or more details of the patient. In some embodiments, the device and/or each receptacle may have machine-readable indicia. Suitable forms of machine-readable indicia include, for example, bar codes, datamatrices, and electronic data storage elements such as RFID tags. Devices carrying such machine-readable indicia allow for unique labelling of tissue samples, which permits reliable identification of the sample and improved auditability throughout the processing of the samples.

In one aspect the invention provides a tissue separation and collection device comprising at least one machine readable data storage element. That allows data relating to the medical procedure and harvested samples to be entered into a data storage system and reliably associated with other information held, the information subsequently being reliably retrievable at other remote locations. That may permit data relating to a tissue collection procedure to be collected, for example one or more items of data relating to the patient, time and/or date, location within the body cavity at which the sample was collected, and details of the clinician. Optionally the machine readable storage element may be writable. In that way it may be possible to record on the device unique identifying information relating to the patient and/or to individual samples collected from the patient. Where, optionally, the samples are to be delivered within the device to another location, for example to a pathology department for examination, the use of such information storage elements enables the information to accompany the sample(s) without any need for the information to be transferred to another container, thus ensuring that reliable information concerning the sample(s) is received at the remote location.

The device may be arranged to indicate correct or incorrect positioning of the filter receptacles. That may be advantageous in embodiments with more than on filter receptacle and especially where there is provision for a bypass pathway along which fluid would flow without passing through a filter receptacle. In an embodiment described below, coloured directional indicators are provided on the circumferential wall. Such arrangements can for example be used in combination with illumination devices. For example, illumination directed towards the circumferential wall may impinge upon an indicator (indicating incorrect positioning) or upon an unmarked region of the circumferential wall between the indicators (confirming correct positioning).

In certain embodiments of the invention provision may be made for illumination of collected samples. Illumination may, if desired, be achieved by illumination through the viewing window or through adjacent portions of the lid of the device. It may be preferable, however, for the device to be illuminated by a laterally located source of illumination. In certain embodiments an illumination device can provide illumination to said circumferential wall, sufficient of the light being transmitted through the wall for illumination. It is unnecessary for the wall to be transparent to relevant light wavelengths, as a relatively diffuse transmission of light may be sufficient to enhance visualisation of tissue in the receptacle.

In one embodiment, the device may comprise one or more lateral windows for permitting illumination to enter the device. The lateral illumination windows may comprise simple apertures, or may further comprise a transparent element, for example a transparent membrane, that is transparent to light of desired wavelengths. In some such embodiments there may be a plurality of illumination windows, for example the number of illumination windows may be the same as the number of collection receptacles. It will be appreciated that, where they are present, the location of the illumination window(s) and the illumination supplied thereto should be such that the illumination reaches those parts of the device where illumination is desired, and in particular the receptacles. That may be achievable by forming those parts of the device through which illumination is required such that they provide adequate light transmission, for example they may be formed of materials that are transparent or translucent. Thus, at least some selected parts of the circumferential wall of the device and at least some selected parts of the internal structure, for example at least a part of the structure in the vicinity of the receptacles, may be transparent or translucent, to light of the relevant wavelengths. It may be preferable for the relevant parts of the structure to be translucent, whereby the light entering the receptacles is diffuse, which is found to enhance visualisation of the samples within the receptacles. In some embodiments, the illumination may be utilised also to show more clearly (especially when the device is used in an operating theatre where light levels are low) whether the device is positioned correctly for tissue sample collection. For example, the device may include a light filter that is operable to filter incident light that is directed at the lateral illumination window or windows, whereby the receptacles are lit by light of a colour that is indicative that the device is not set in the position for tissue collection. Thus, in practice, the filter may be so arranged that the receptacles are lit with coloured, for example red, light when the device is not correctly set for tissue sample collection, whilst the receptacles are lit with light of a different colour or white light when the device is correctly set for use. In practice, the use of visible light may be advantageous, but if desired other light sources may be used, for example ultraviolet or infrared light.

Each of the illumination windows may serve to deliver filtered light of a selected colour when it is in register with the illumination source, in contrast to light of a different perceived colour (including white light) which is delivered through a light-transmitting portion of the circumferential wall of the device when a receptacle is in register with the source of illumination. In other embodiments, however, the illumination windows might be movable relative to the receptacles so that the illumination windows are able to deliver light both when they are in register with a receptacle and when they are not in register with a receptacle. In that alternative embodiment, a filter member is advantageously located to provide filtering only at window locations where the window is not in register with a receptacle.

The invention also provides a kit comprising a tissue separation and collection device according to this invention having lateral illumination windows and an illumination device for providing illumination to said lateral illumination window or windows of the device. The kit may further comprise at least one mounting member for so mounting the illumination device and the tissue separation and collection device relative to one another that the illumination device, in use, directs incident light towards circumferential wall of the separation and collection device. The light may be directed selectively through a said lateral illumination window. The device is advantageously so arranged that the light is selectively directed through the windows, and through an associated light filter, when the device is located in a non-collection position in which fluid is being passed through the device without filtering. The generation of the filtered light can then provide a warning signal by providing illumination in a particular colour dictated by the filter, for example, red light may indicate the non-collection position. Light directed otherwise into the device through a lateral wall when a collection receptacle is aligned with the light source will then be of a different colour, providing confirmation that the device is arranged in the sample collection configuration.

It is possible in principle for the position of the illumination windows relative to the collection receptacles is adjustable. In an illustrative embodiment, in a first position, an illumination window may be in register with a said receptacle. The device is then preferably so arranged that, when in a further position in which the or each illumination window is circumferentially located between receptacles rather than in register therewith, the nature of the illumination of the receptacles is different, for example, the illumination may be in a different colour as compared with the first position, or the illumination may be reduced or eliminated.

Advantageously at least those internal parts of the device which, in said first position, are located between an illumination window and a receptacle are arranged to be able to transmit light of the relevant wavelength.

Where illumination is used, the illumination device may advantageously be a torch, which may advantageously be configured to generate a narrow beam of light into the device. That is advantageous in permitting illumination of sample(s) whilst otherwise minimising stray light that could otherwise be distracting for staff working in low light levels, such as those typical in an operating theatre during endoscopic procedures.

The invention also provides an apparatus for use in collecting tissue from an effluent stream in which tissue is entrained in a carrier fluid, comprising a tissue collection device and an illumination device, the tissue collection device comprising at least one tissue retention location, a viewing window for permitting viewing of tissue retained in said tissue retention location, and an illumination window located to permit illumination of tissue retained in said tissue retention location, the apparatus further comprising a mount, wherein the mount is configured and dimensioned for receiving the tissue collection device and so positioning it relative to the illumination device that said tissue retention location is, in use, illuminable by illumination from the illumination device. Advantageously, in a said apparatus, the tissue collection device has two or more tissue retention locations, and the tissue retention locations are movable relative to the illumination device to enable one or more said tissue retention location to be selectively illuminated. Advantageously, the tissue collection device has two or more tissue retention locations and a plurality of illumination windows, and the tissue retention locations and illumination windows are movable relative to the illumination device to enable one or more of said tissue retention locations to be selectively illuminated, through a wall of the device or via a said illumination window. The illumination windows and tissue retention locations are preferably movable together. Optionally the illumination windows are movable relative to the tissue retention locations. Advantageously, the tissue collection device further comprises at least one light filter for filtering light received through the illumination windows. The light filter may advantageously be arranged to indicate a given operative condition of the device, for example by generating a different illumination wavelength when that condition is present. Endoscopic procedures are often carried out in operating theatres or other rooms with low light levels.

The apparatus of the invention offers the advantage or providing improved visualisation of removed tissue samples by the clinician. This facilitates faster and more reliable checking of the receptacle to ascertain whether, and how much, tissue has been collected.

The device may be made of any suitable material. Suitable materials include, but are not limited to polymer materials, for example polymer materials selected from polyethylene, polypropylene, polyamide, polyethylene terephthalate, polyvinylchloride, polycarbonates, acrylonitrile butadiene styrene, acrylates.

The device can be manufactured by any suitable method. It is preferably manufactured using injection moulding, which enables close fitting parts to be made with accuracy and reliability.

In accordance with the method of the invention, the effluent stream is advantageously drawn through the device by means of suction applied to the outlet port. Advantageously, the effluent stream is optionally intermittently deflected from said upward direction of travel into a bypass pathway from which it is withdrawn through the outlet aperture without passing through said filter member. For example, said deflection may be effected by means of relative rotation of a first part of the trap device relative to a second part of the trap device.

The device of the invention may be located in a fluid transport line that communicates between a suction source and a conduit of an instrument. It will therefore be appreciated that the trap is located outside the body of the patient. If desired, however, where the instrument has an operating or control portion which remains outside the patient's body during the sample collection procedure it may be possible for the device to be incorporated into that operating or control portion.

In practice, the inlet aperture and/or the outlet aperture will generally communicate with structures which are suitable for mounting of tubing in fluid communication with the inlet aperture and outlet aperture respectively. For example, the inlet aperture may be in connection with an inlet port. The inlet port may be of any suitable configuration and dimensions provided that it is suitable for receiving in sealing connection a suitable fluid feed tubing and defines a channel for communication to the inlet aperture of fluid received through the feed tubing. Analogously, the outlet aperture may be in connection with an outlet port. The outlet port may be of any suitable configuration and dimensions provided that it is suitable for receiving in sealing connection a suitable fluid exhaust tubing and defines a channel for communication from the outlet aperture of fluid from the device into the exhaust tubing. The inlet port and/or the outlet port may each be in the form of a respective hollow cylindrical structure extending outwardly, for example downwardly, from the lower wall, the cylindrical structure defining an internal channel that at one end is in communication with the respective aperture in the lower wall and at the other end is open. At least one, and optionally both, of the inlet port and the outlet port may expediently comprise a hollow cylindrical structure extending perpendicularly downwards from the lower wall. In practice, the length of the inlet port and outlet port will in each case be sufficient for the mounting of flexible tubing, and may for example be at least 5 mm in length, for example from 5 mm to 20 mm, or 5 mm to 15 mm in length. Where present the inlet ports and outlet ports are dimensioned and configured for mating with suction lines of standard diameter used in medical procedures. The inlet port and/or outlet port are furthermore arranged to provide effective sealing connection with such suction lines in the form of, for example, flexible polymer tubing of kinds conventionally used in a medical environment, including without limitation tubing of silicone, PVC, polyester or the like. The invention includes a kit comprising a device of the invention and an elongate flexible tubing. In some arrangements it may be expedient for the tubing to be of length 300 to 600 mm tubing. In other embodiments, a shorter tubing may be used, for example of length less than 300 mm, for example 50 mm to 250 mm. In some embodiments it may be desirable to use tubing of sufficient rigidity that the tubing can support the device in a raised position. Illustrative of suitable tubing are any that are typically used in a medical facility, for example silicone tubing and PVC tubing. For example, a PVC tubing may expediently be used in those embodiments where it is desired that the tubing may at least partly support the device in a raised position.

In a particular embodiment of the invention, the device is provided in a suction line that is connected to a scoping device for gastrointestinal examination, for example an endoscope, enteroscope, colonosope, gastroscope or sigmoidoscope. The device may be suitable particularly for use in colonoscopy procedures where collection of excised polyps for subsequent pathological analysis is carried out. The device may, however, be useful in any procedure in which tissue is to be collected for further analysis, for example, without limitation, intrauterine procedures to resect and remove tissue including submucous myomas, endometrial polyps, endoscopic mucosal resection of Barrett's oesophagus and organ biopsies as well as the removal of infected material from body cavities or organs.

Whilst the present invention has been described and illustrated with reference to particular embodiments, it will be appreciated by those of ordinary skill in the art that the invention lends itself to many different variations not specifically illustrated herein. By way of example only, certain possible variations will now be described with reference to the accompanying drawings.

4. BRIEF DESCRIPTION OF DRAWINGS

FIG. 3 is a plan view of the device of FIG. 1 from above;

FIG. 4 is an exploded view of the device of FIG. 1;

FIG. 5 is a section through the device of FIGS. 1 to 4 along the line A-A in FIG. 3

FIG. 6 is a section through the device of FIGS. 1 to 5 along the line B-B in FIG. 3;

FIG. 9 is a perspective view from below of the part of FIG. 8;

FIG. 10 is an exploded view of a device according to a second embodiment of the invention;

Figure 11:
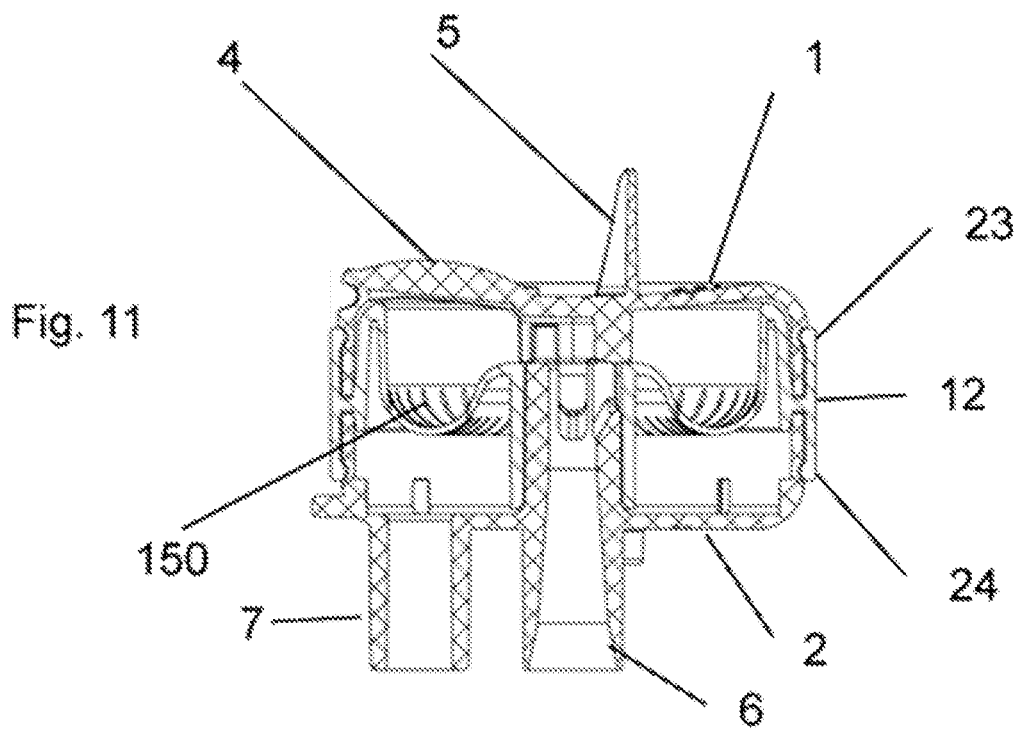
FIG. 11 is a section through the device of FIG. 10.
Figure 12:
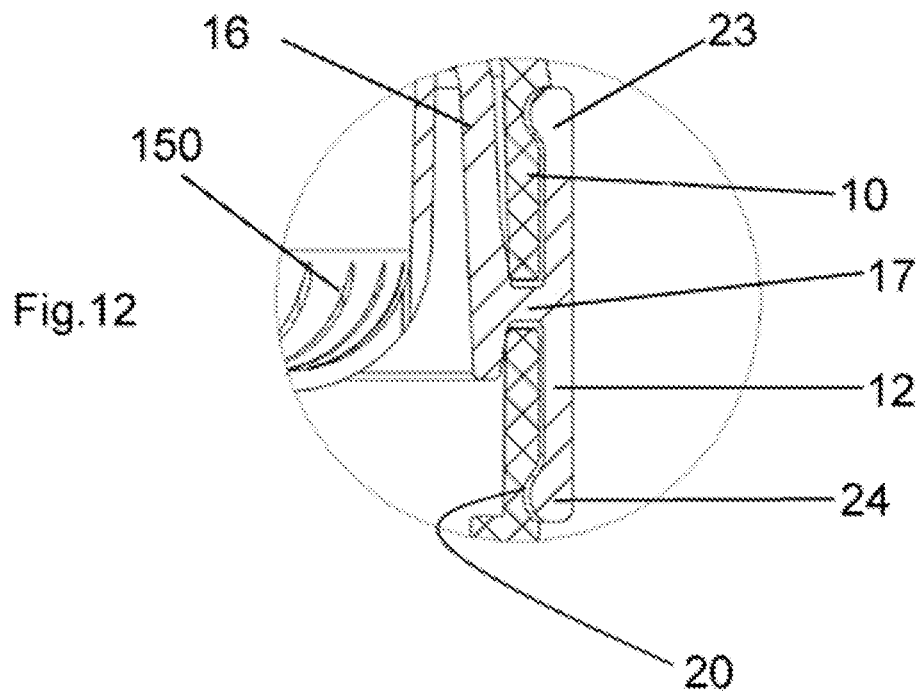
Figure 13:
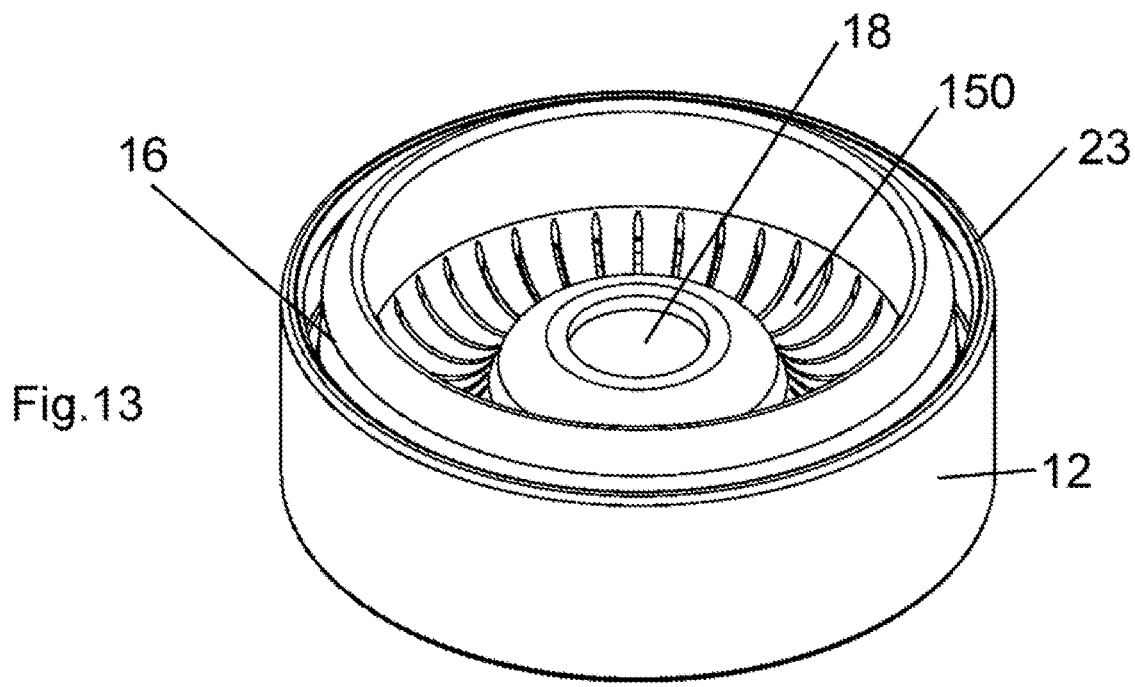
Figure 14:
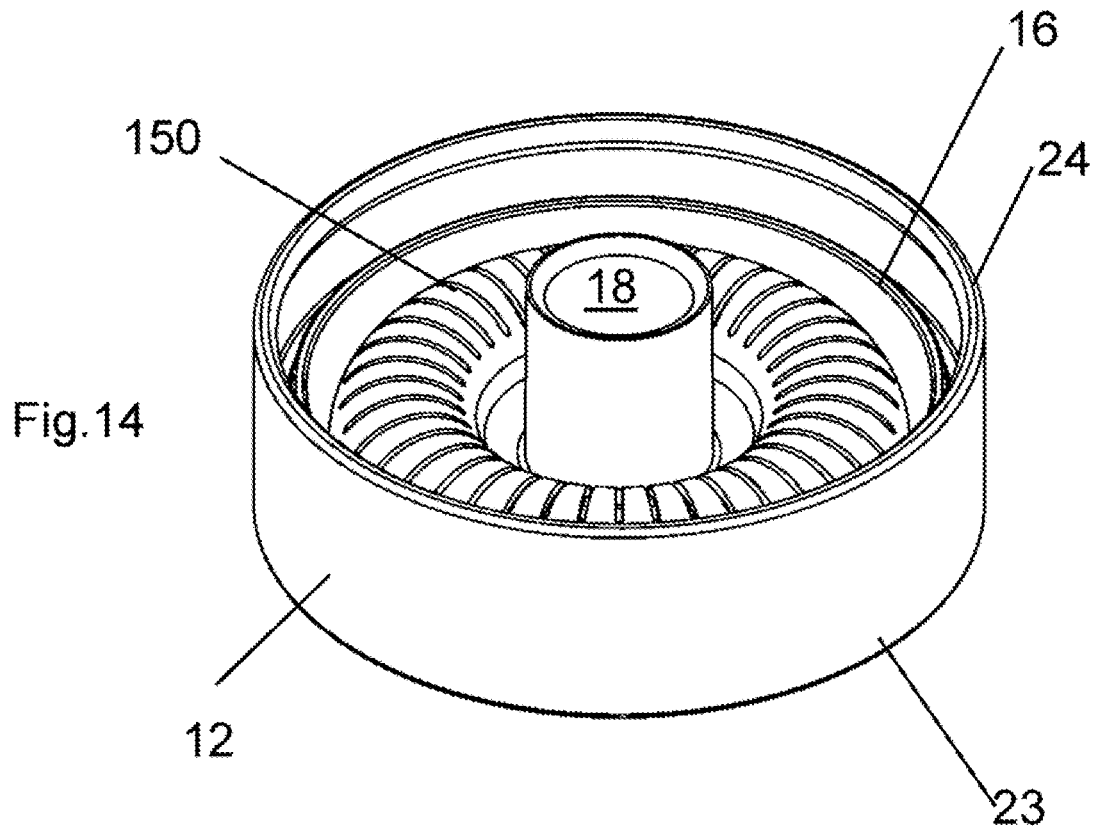

FIG. 12 shown in section a detail of the seal of the device according to FIGS. 10 and 11;

FIG. 13 is a perspective view from above of a part of a device according to the second embodiment of the invention;

FIG. 14 is a perspective view from below of the filter member of FIG. 13

Figure 15:
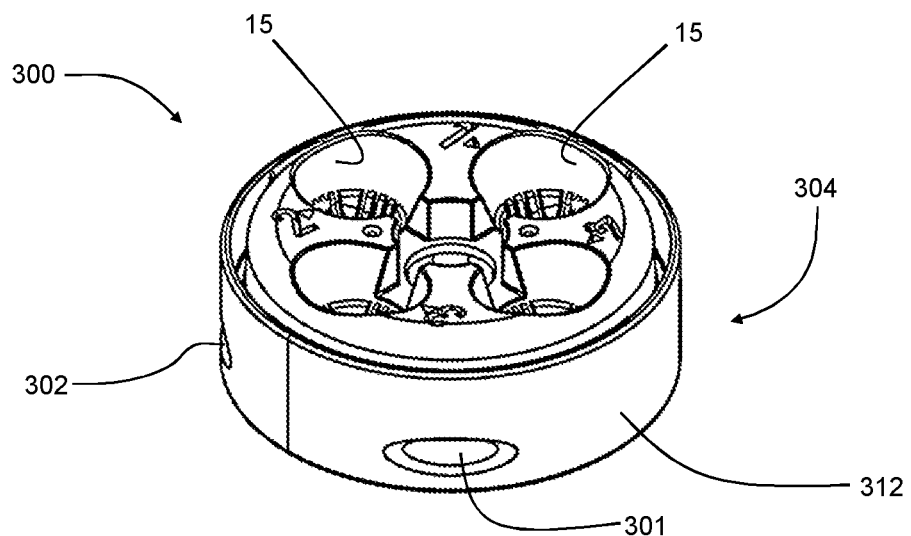
Figure 16:
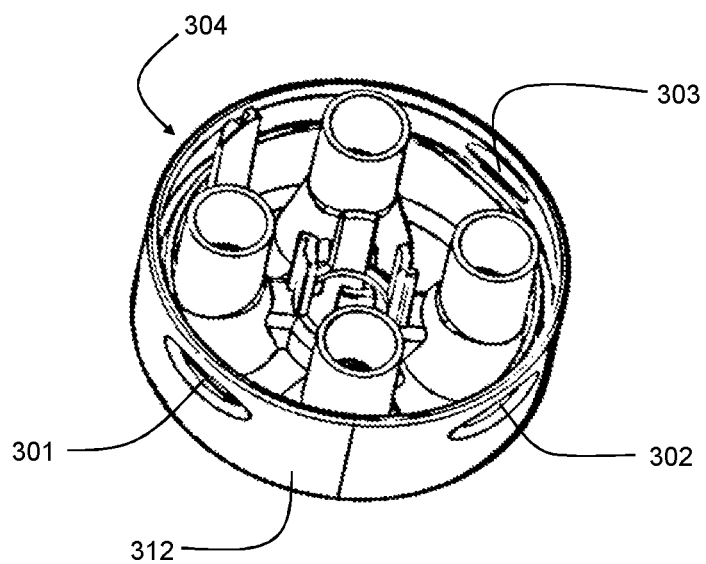
Figure 17:
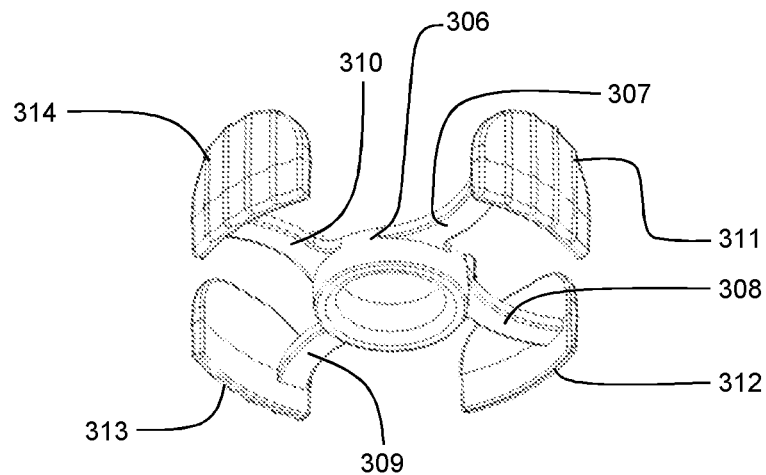
Figure 19:
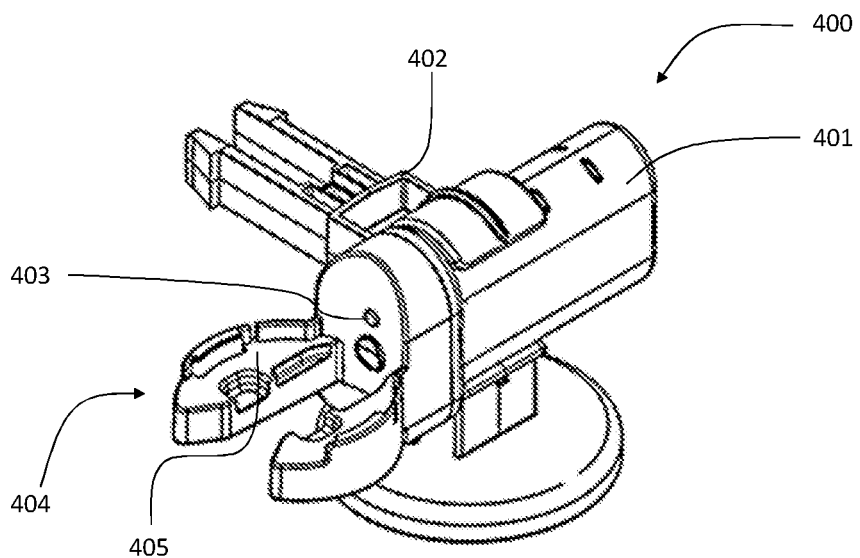
Figure 18:
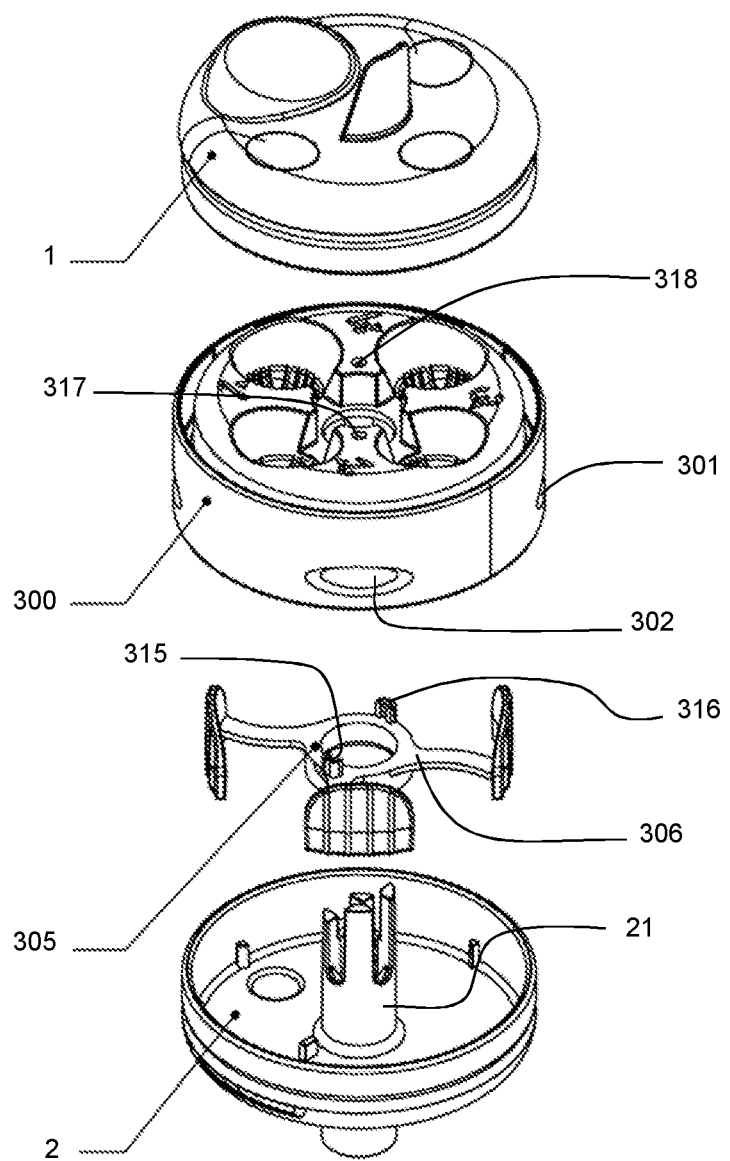
Figure 20:
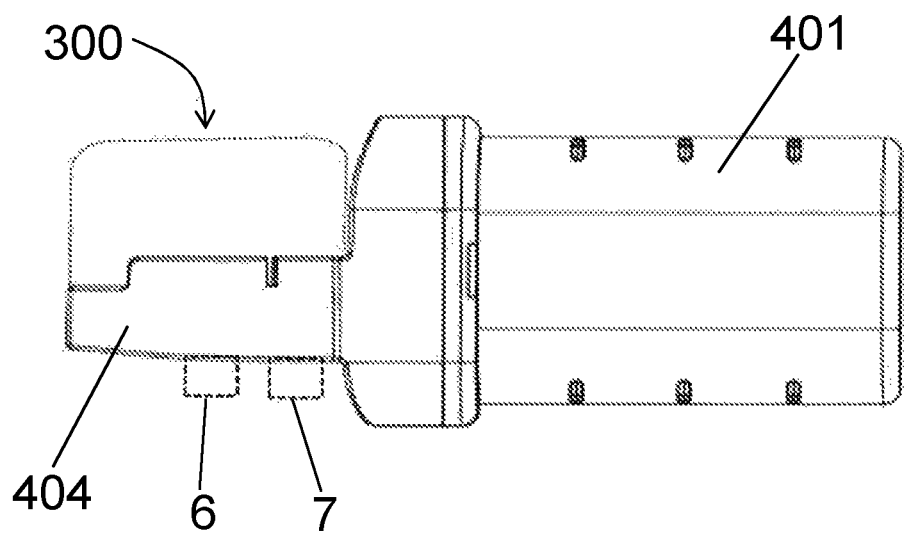
Figure 21:
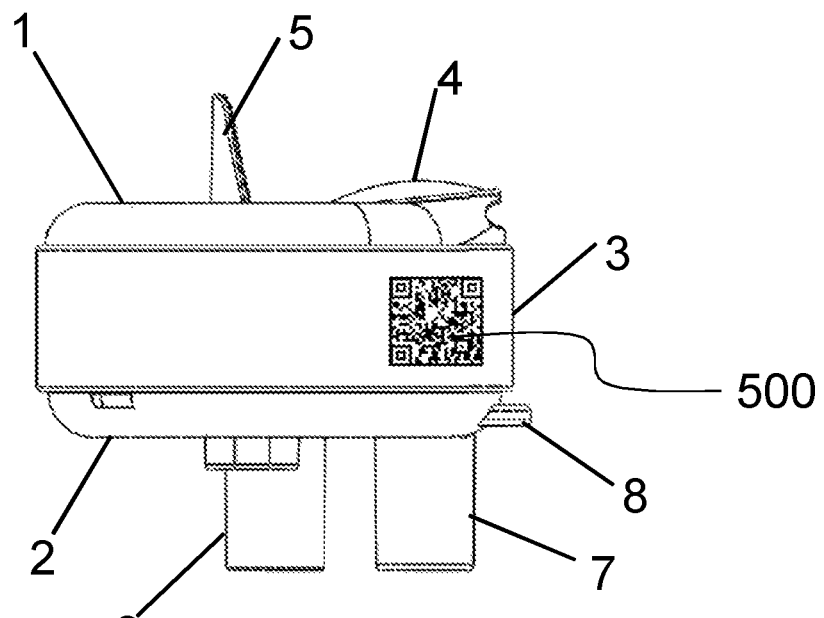
Figure 22:
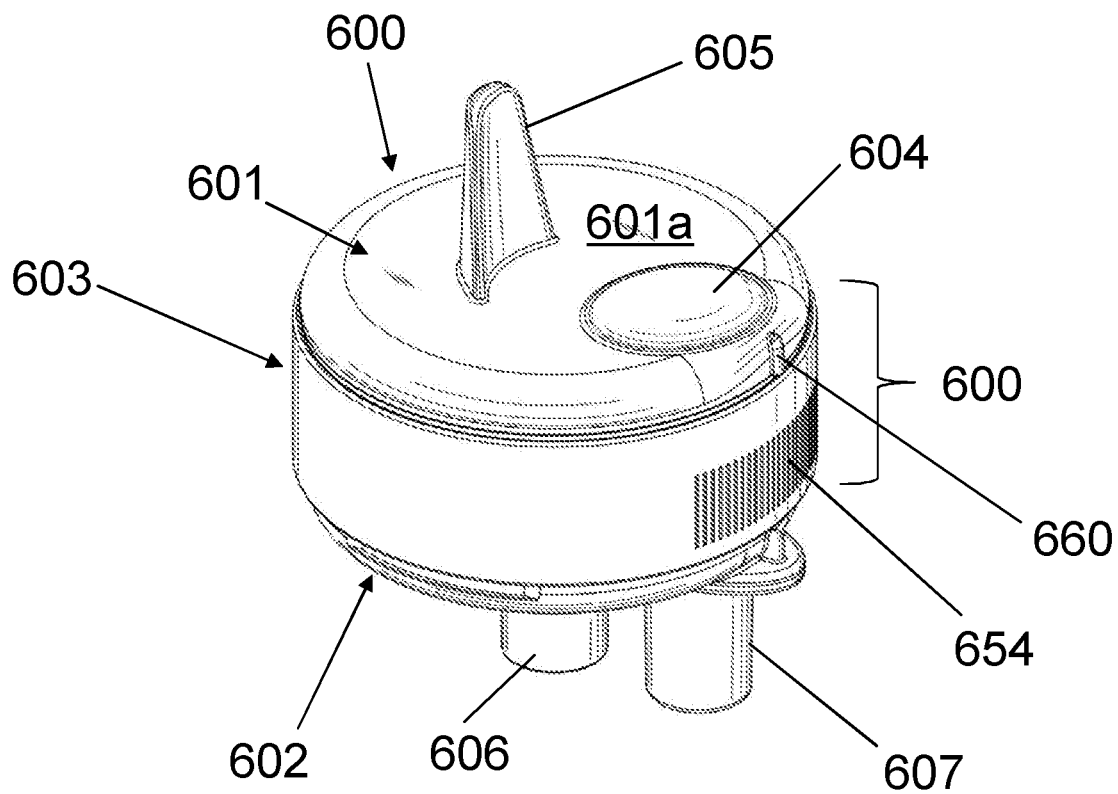
Figure 23:
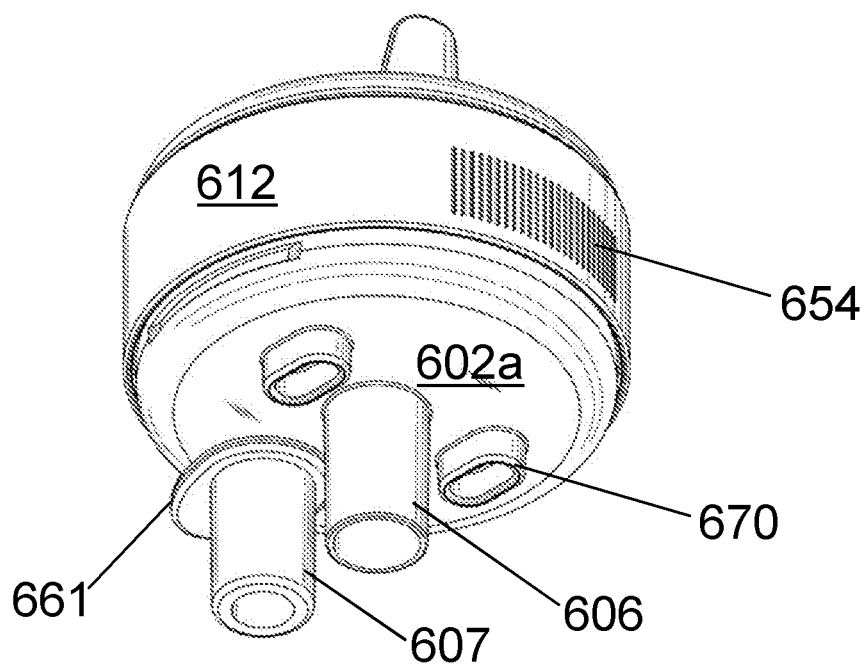
Figure 24:
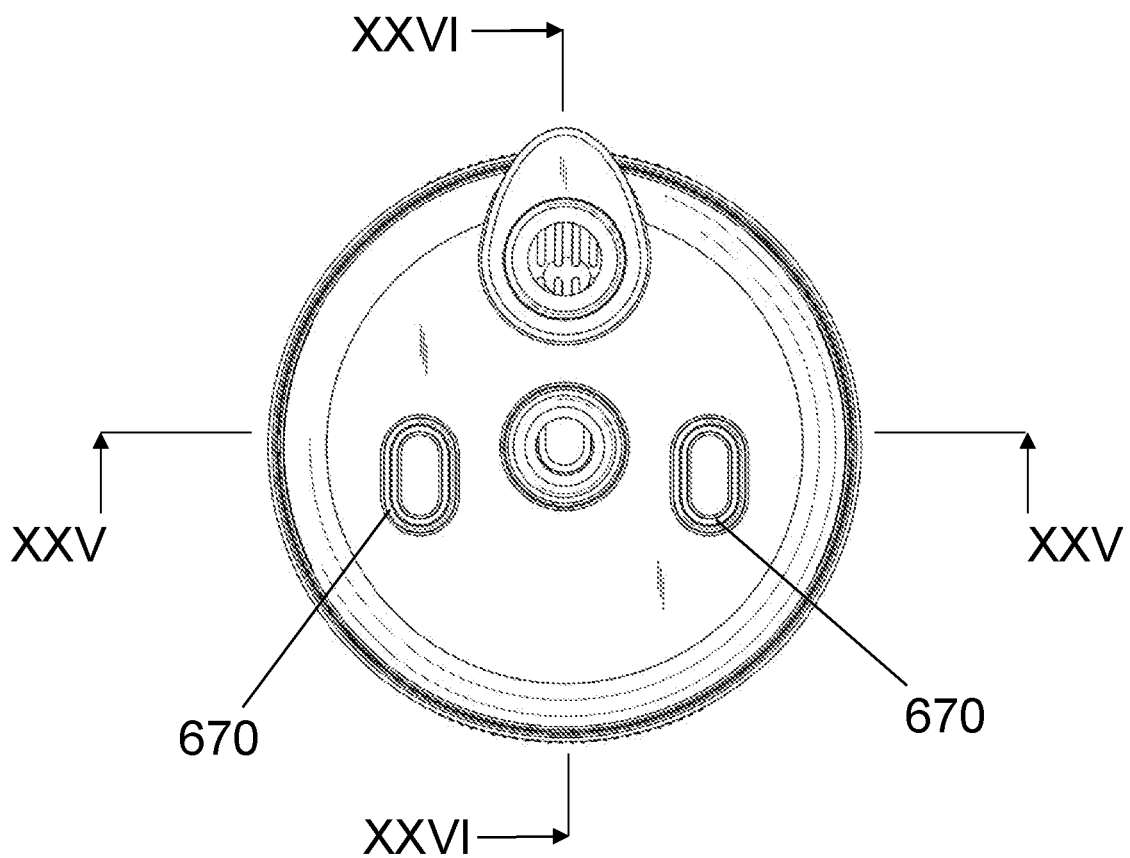
Figure 25:
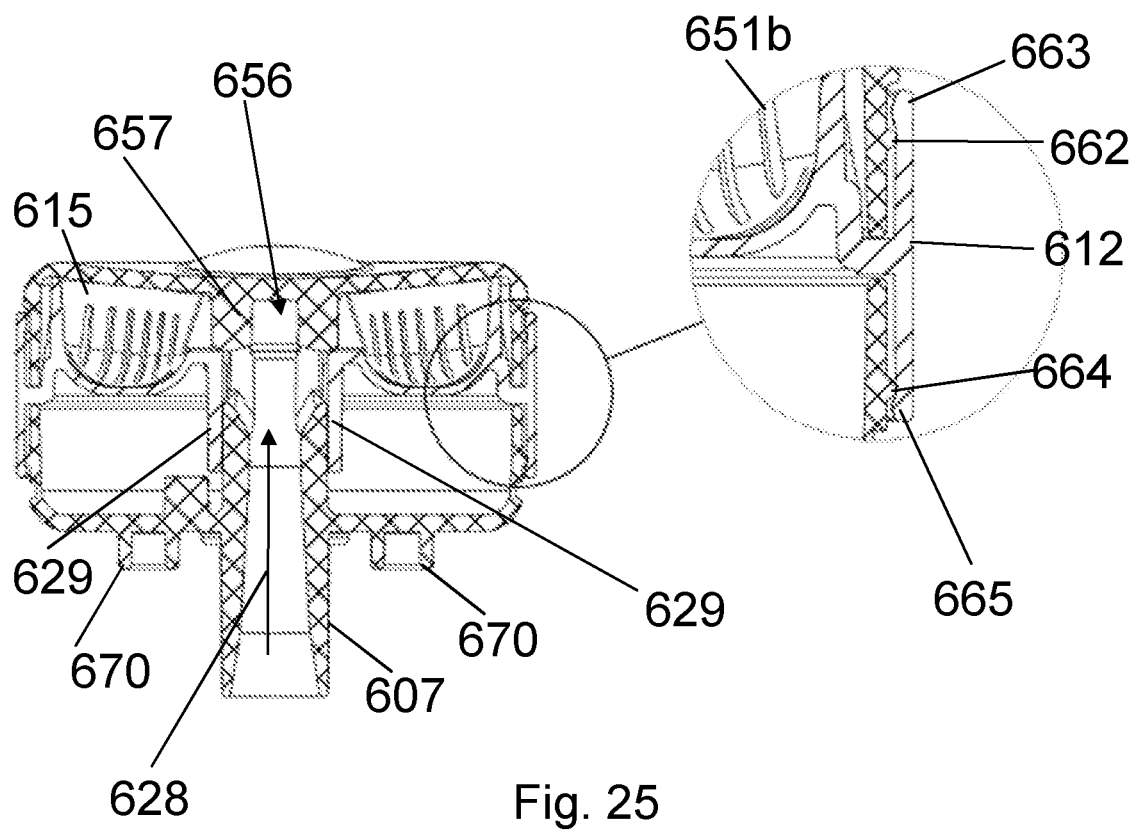
Figure 26:
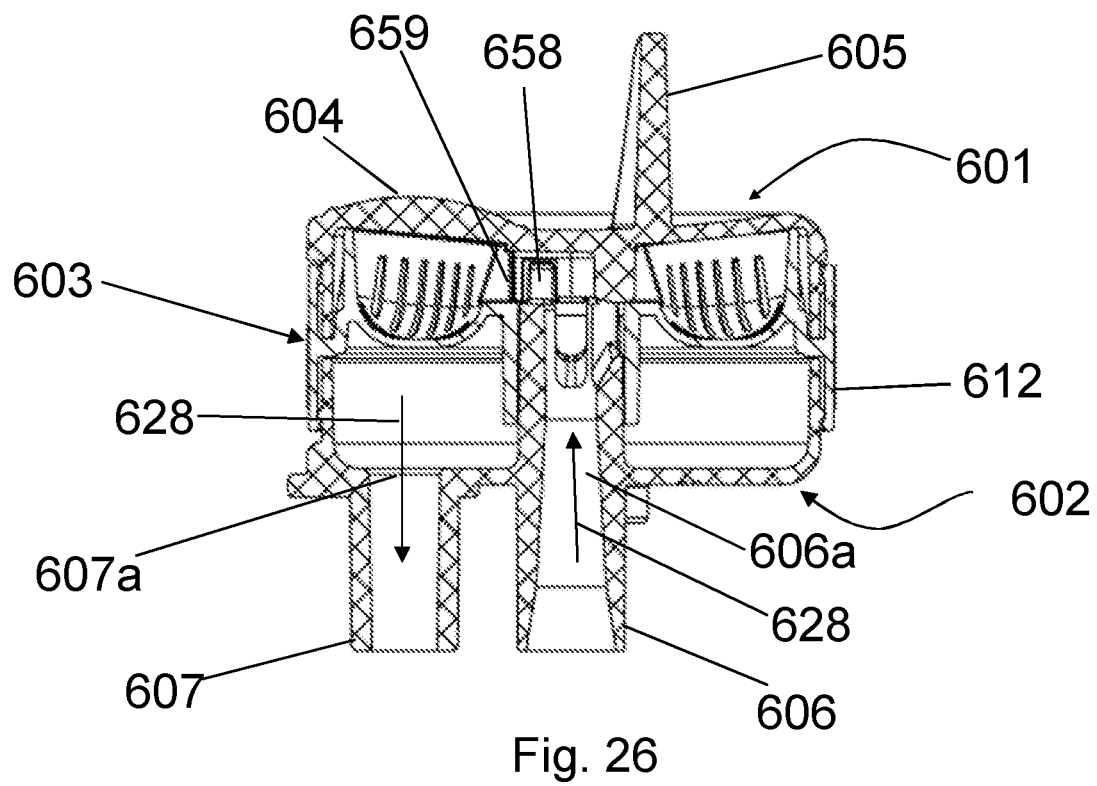
Figure 27:
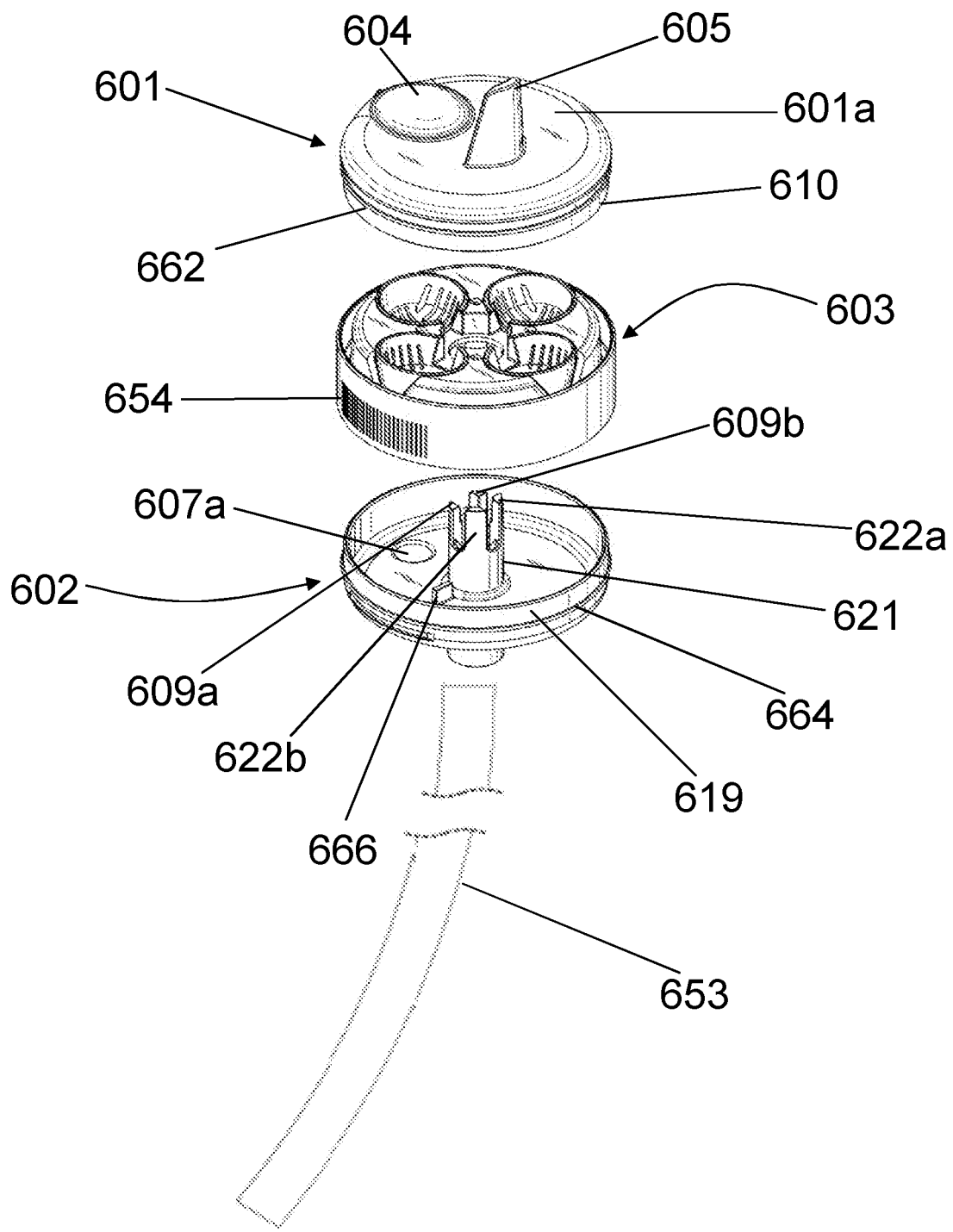
Figure 28:
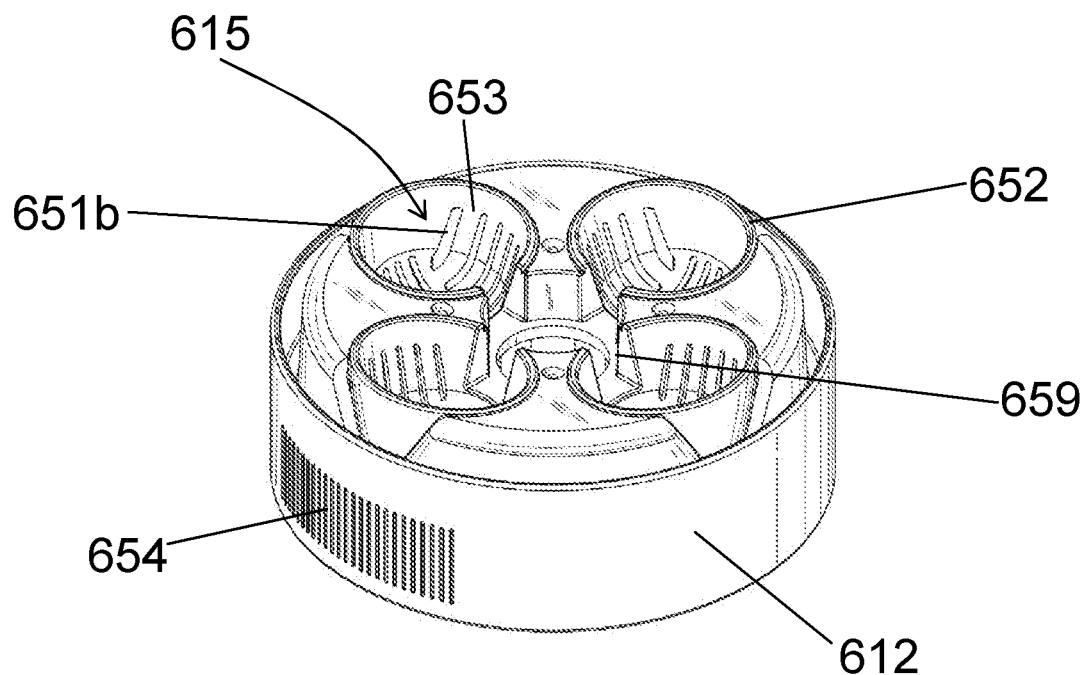
Figure 29:
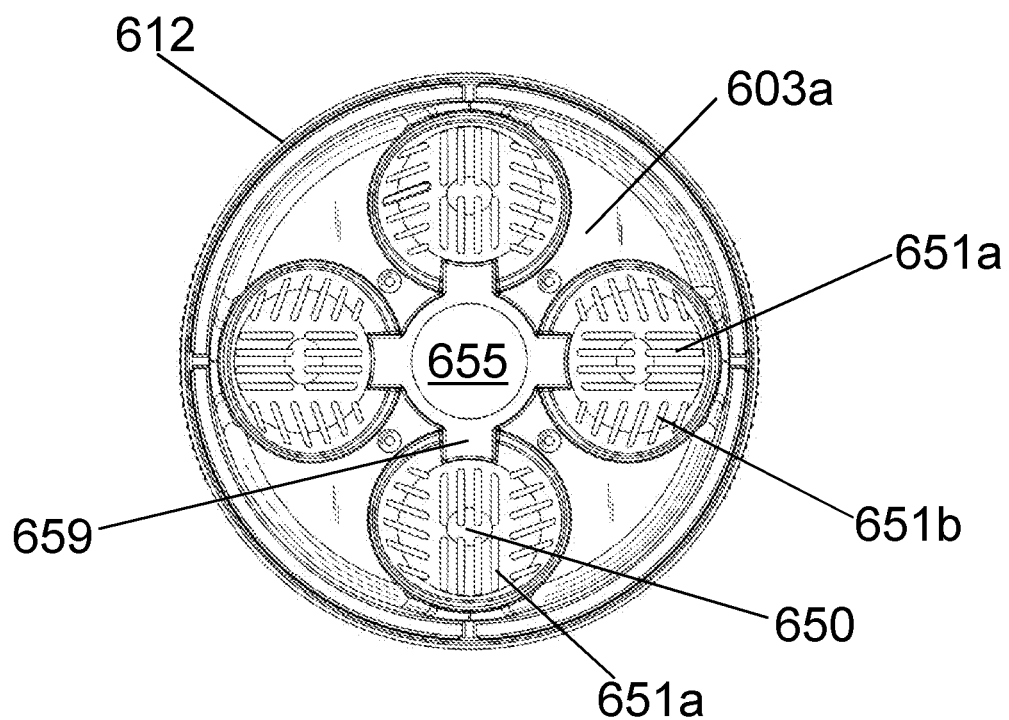
Figure 30:
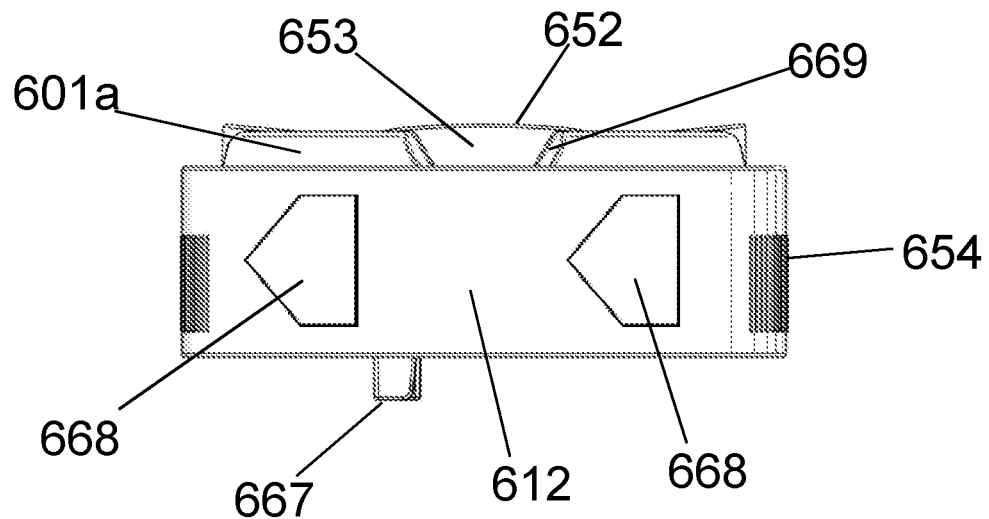
Figure 31:
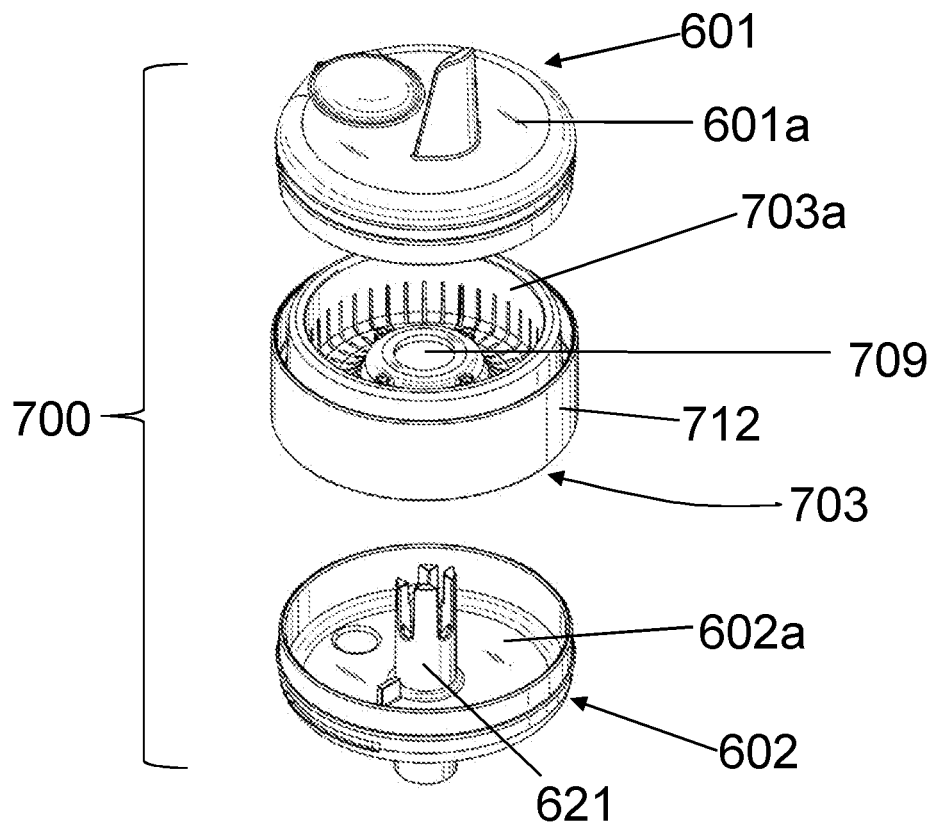
Figure 32:
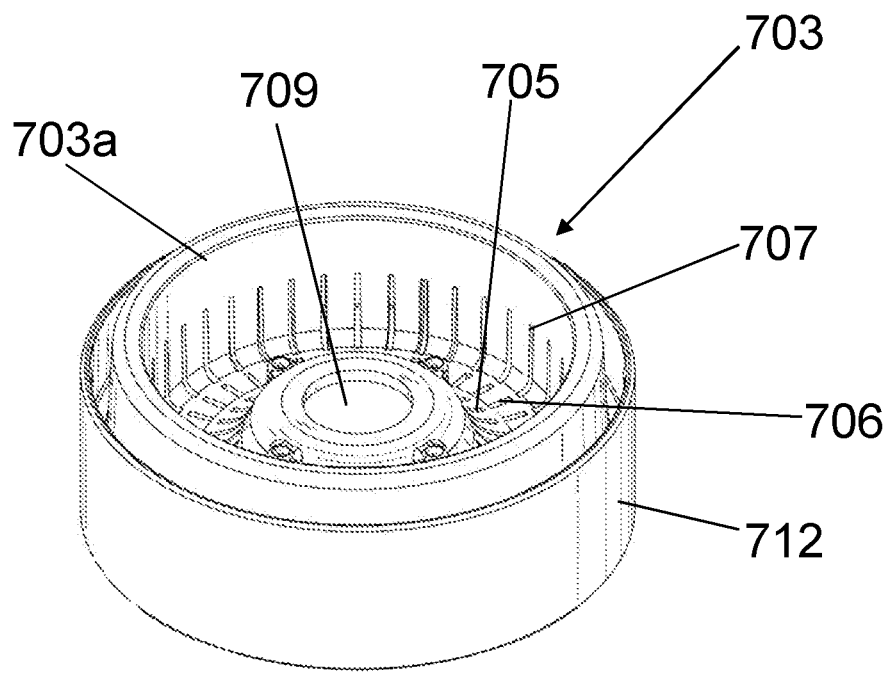
Figure 33:
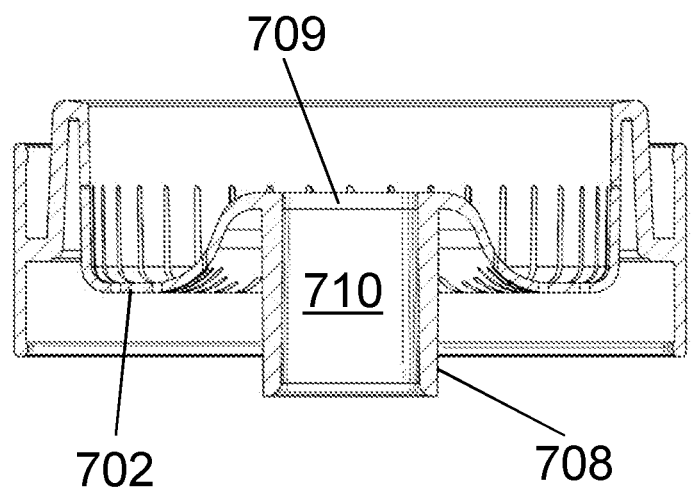

FIG. 15 is a perspective view from above of a part of a device according to a third embodiment of the invention;

FIG. 16 is a perspective view from below of the part of FIG. 15;

FIG. 17 is a perspective view of a light filter member for use in the device of the third embodiment;

FIG. 18 is an exploded view of the third embodiment including the parts shown in FIGS. 15 to 17;

FIG. 19 is a perspective view of an illuminating device for use in a kit comprising a device of the invention;

FIG. 20 shows a portion of the illuminating device of FIG. 19 and further indicates the location of a tissue collection device mounted in cooperative engagement with the illuminating device;

FIG. 21 shows an embodiment of the device of the invention in which a data storage element is present;

FIG. 22 is a perspective view of a further embodiment of device according to the invention;

FIG. 23 is a perspective view from below of the device of FIG. 21;

FIG. 24 is a plan view of the device of FIGS. 23 and 24 from below;

FIG. 25 is a section through the device of FIGS. 22 to 25 in a first direction indicated in FIG. 24;

FIG. 26 is a section through the device of FIGS. 22 to 25 in a second direction indicated in FIG. 24;

FIG. 27 is an exploded view of the device of FIGS. 22 to 26 with a portion of tubing;

FIG. 28 is a perspective view of a separation member suitable for use as part of the device of FIGS. 22 to 27;

FIG. 29 is a plan view of the separation member of FIG. 28;

FIG. 30 is a side view of the separation member of FIGS. 28 and 29;

FIG. 31 is an exploded view of a further embodiment of device of the invention which is a variant of the embodiment of FIGS. 22 to 27;

FIG. 32 is a perspective view from above of the separation member of the device of FIG. 30;

FIG. 33 is a section through the separation member of FIG. 31;

5. DESCRIPTION OF EMBODIMENTS

Figure 1:
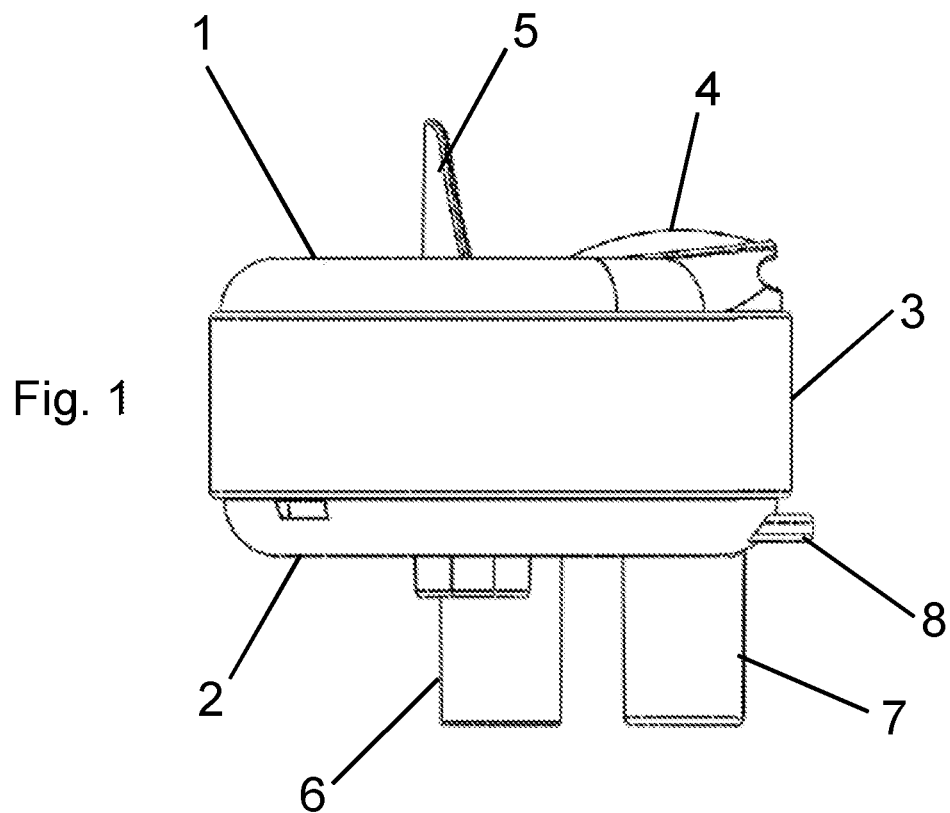
FIG. 1 is a side view of a device according to a first embodiment of the invention.
Figure 2:
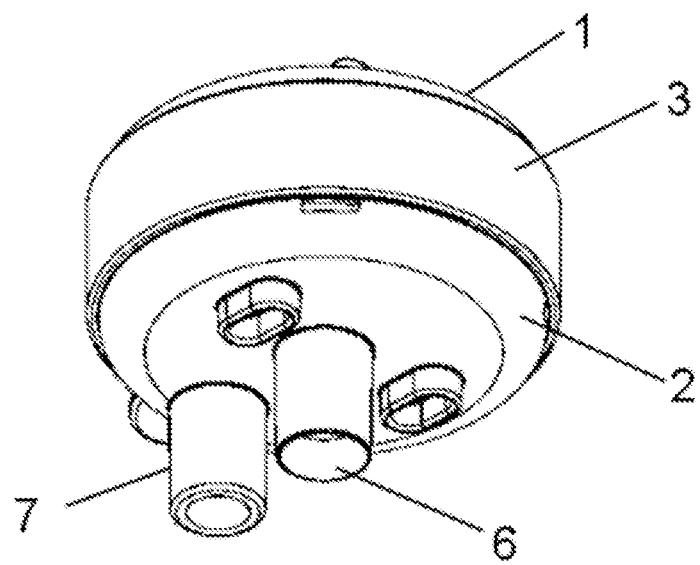
FIG. 2 is a perspective view of the device of FIG. 1 from below.
Figure 7:
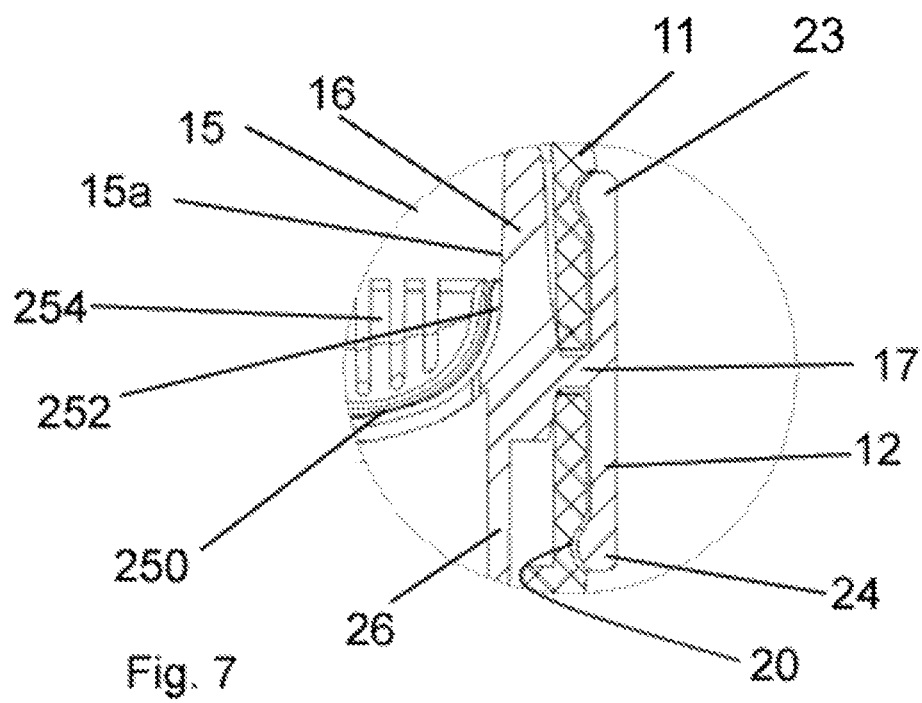
FIG. 7 shows a detail of the device seal of the device according to FIGS. 1 to 6.
Figure 8:
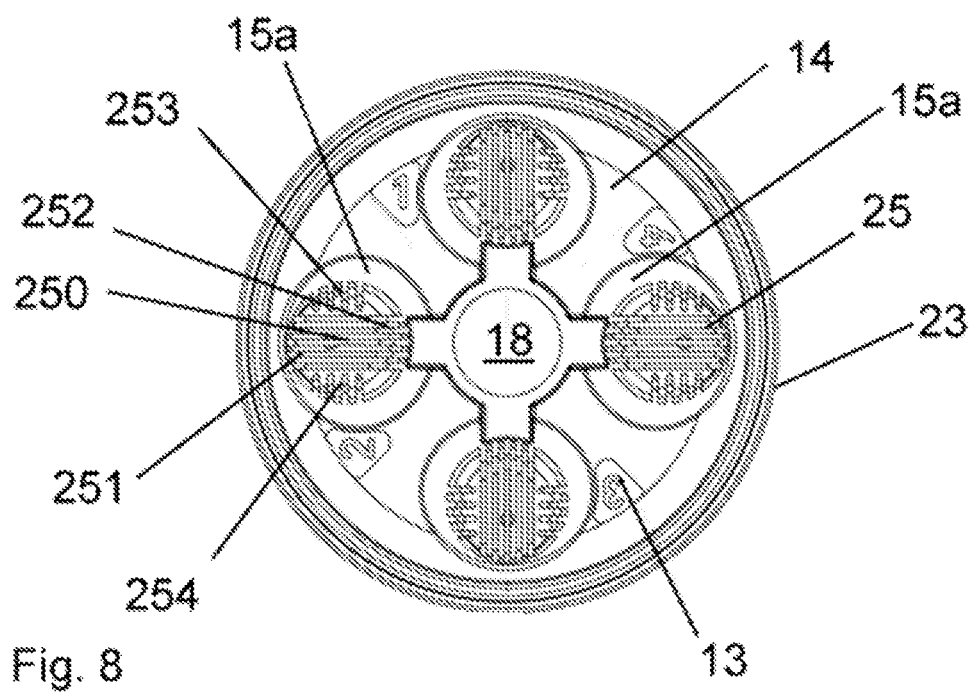
FIG. 8 is a plan view of a part of the device of FIGS. 1 to 7.

With reference to FIGS. 1 to 3, in a first embodiment the device has a lid member 1, a base member 2, and a filter member 3 located between the lid member and the base member. The lid member and the base member are each removably attached to the filter member 3 in snap fit fashion.

The lid member 1, which may be generally transparent or semi-transparent has a transparent viewing window 4 in the form of a magnifying lens and an adjacent projection 5 which serves to reduce access of stray light. The base member 2 has a centrally located inlet comprising an inlet aperture 6a which is connectable to an upstream suction line by an inlet port 6 and an eccentrically located outlet aperture 7a that is connectable to a downstream suction line by exit port 7. A tab 8 is provided on the base member 2. The base member 2 and lid member 1 are rotatable relative to the filter member 3, and cooperating locking means is provided between central regions of the lid member and base member such that the lid and base members co-rotate. The cooperating engagement is not visible in FIGS. 1 and 2. With reference to FIG. 3, the cooperating locking means comprises a pair of projections 9a, 9b extending upwardly from a central region of base member 2 which engage in a pair of apertures located in a central region of lid member 1. These apertures, which serve as air vents when the base member is removed, are sealed by the pair of projections 9a, 9b when the device is capturing tissue samples. The air vent apertures open when the base member is removed to allow placement of the lid member 1 and filter member 3 into a formalin pot and enable air to escape as formalin enters the device, thereby avoiding entrapment of air which could adversely affect preservation of the tissue.

FIG. 4 shows an exploded view of one form of device according to FIGS. 1 to 3. In this exemplary embodiment, the device is intended to allow collection of four discrete tissue samples.

The lid member 1 includes a generally planar circular upper wall with a bevelled lateral portion which together form an upper wall 1a of the device, and from which depends an annular flange 10. A circumferentially extending groove 11 is provided in a top region of the flange 10.

The separation member 3 has an outer annular wall which forms a circumferential wall 12 of the device and encloses a filter member 14 having an upper surface in which are located four recessed portions 15 which, as further described below, act in use as filter receptacles selectively usable in series to collect up to four separate tissue samples. The recessed portions (filter receptacles) 15 are distinguished from one another by appropriate indicia 13, for example in the form of consecutive numbers 1 to 4 or letters A to D. The filter member includes a depending flange 16 (FIG. 5) which extends circumferentially within and essential concentrically with the wall 12 forming a generally annular void between the wall 12 and flange 16. A circumferentially extending ring 17 is provided between and connecting the wall 12 and flange 16 at a position intermediate the top and bottom extremities of the member 3. In the embodiment shown the ring 17 is integrally formed with the wall 12 and flange 16 but other forms of connection are possible. A through hole 18 is provided centrally in filter member 3.

Base member 2 includes a generally planar circular wall forming a lower wall 2a of the device, which cooperates with the wall 12 and upper wall 1a to form a housing which, when assembled, is closed with the exception of the inlet aperture 6a and outlet aperture 7a. From the periphery of the lower wall 2a extends upwardly an annular flange 19, and a circumferentially extending groove 20 is provided in a lower region of the flange 19. An upwardly extending hollow cylindrical structure 21 is located in a central region of the base member 2 to provide fluid communication between the inlet port 6 and the interior of the device. The structure 21 has a lower portion which is annular in structure and four projections extending upwardly therefrom. The four projections comprise two pairs, with a first, shorter pair 22a, 22b, whilst second pair 9a, 9b are longer than the first pair and serve to engage corresponding air vent apertures in lid member 1 as previously described. The projections cooperate with structures provided on the separation member and lid member selectively to define a fluid flow path. By selecting a given juxtaposition of the separation member 3 relative to the co-rotating lid and base members 1, 2, a fluid flow path may be selected as between a fluid flow path into a selected one of the filter receptacles and a fluid flow path which allows the fluid to flow directly to the outlet port 7 without passing through any of the filter receptacles.

With reference to FIG. 5, the wall 12 of separation member 3 has circumferentially extending enlarged edge regions 23 and 24 at its upper edge and lower edge respectively. Each of the recessed portions 15 is of the same construction. Each includes an upper smooth wall 15a which extends circumferentially around the upper region of the recessed portion 15 except for the region adjacent to the central axis of the separation member, and slopes downwardly to a basket 25 in which the tissue is to be filtered and collected. The basket has a fluid-permeable floor having a multiplicity of slots, described in more detail further below, through which carrier fluid can drain. Under each basket 25 is provided a downwardly extending channel 26 which is so dimensioned and configured that, when the respective recessed portion is selected, the corresponding channel 26 is in register with, and communicates with, the outlet port 7 so that the filtered fluid is withdrawn through the outlet after filtration. The lid member 1 comprises a depending structure 27 which includes location channels for receiving the upper portions of projections 9a, 9b and cooperates with the projections 22a, 22b so as to obstruct the space between adjacent projections except for the space between projections 22a and 22b. The filter member 3 is free to rotate in between the lid member and base member, which are in fixed location relative to each other. The filter member 3 can be rotated in a fixed direction into a filtering position in which a fluid flow pathway 28 is formed for delivery of fluid via inlet port 6 and channel 21 into any one of the filter receptacles 15 according to the rotational position of the separation portion 3 relative to the lid member and base member. Four curved curtain members 29 depending from a central region on the undersurface of lid member 1 are so positioned relative to one another that they form segments of a common annulus embracing an upper length of the central through-hole 18 and fit snugly around an upper portion of the hollow cylindrical structure 21 and the protruding projections 9a, 9b, 22a, 22b. The respective spaces between adjacent curtain members 29 serve to cooperate with the projections 9a, 9b, 22a and 22b in certain orientations to form a flow path that extends from the hollow cylindrical structure 21 between said adjacent curtain members 29 into the bottom of base member 2 without passing through any of the receptacles 15.

Alternatively, by rotation of the base member 2 and lid member 1 by 45 degrees, the apertures between curtain members 29 are obstructed by the members 9a, 9b, 22a, 22b respectively, whereby the stream of effluent entering through the inlet port 6 is directed upwardly through the central through-hole 18 and into a selected one of the receptacles 15. In that way, the base member and lid member may be selectively positioned in a non-filtering position in which the fluid flow is diverted underneath the filter member directly to the outlet port without passing through any of the filter receptacles or in a filtering position.

The base member has a number of detents 31 (see FIG. 10) provided at the bottom of the wall 19 on the inner surface thereof. In the device shown in FIG. 4 adjacent detents subtend an angle of 45° at the centre of the base member. The detents provide an indexing arrangement in cooperating with latch 32 with detents corresponding in sequence, when in cooperating relationship with latch 32, alternately to a filtering position or a non-filtering position. As a result the filter member 3 is able to rotate in only one direction, clockwise relative to lid member 1 and base member 2, so that filtration receptacles, numbered with indicia 13 consecutively by sequential identification numbers "1" to "4" in anti-clockwise direction around the filter member 3 are only accessed in strict order "1", "2", "3" and then "4" on clockwise rotation of the filter member.

The indicia 13 may be used as identifiers with which data relating to collection of samples can be associated.

It is an advantage of this embodiment that the effluent stream may optionally be diverted underneath the collection receptacles thereby maximising efficiency of transport of the stream through the device when there is no sample to be collected. Also, the build-up of unwanted small particles within the receptacles is avoided since such particles are withdrawn directly through the outlet port.

With reference to FIGS. 5 to 8, each of the filter receptacles 15 is of the same construction. The slotted basket 25 is designed to centre the biopsy material in the middle of the filtration receptacle for easy viewing and comprises an upper basket portion and lower basket portion comprising a gently concave fluid-permeable base portion 250. The upper basket portion has an outer side wall 251, inner side wall 252 and opposed lateral side walls 253 and 254. Each of the side walls 251, 252, 253 and 254 comprises a multiplicity of protruding parallel elongate members which are inclined downwardly defining between adjacent elongate members and the respective side wall a plurality of parallel drainage channels, which serve to enable drainage to continue even where tissue is lodged against the side wall. Lower end portions of the said elongate members extend beyond the lower periphery of the side walls defining between them elongate apertures. The elongate members on outer and inner side walls 251 and 252 are integrally formed with the base portion 250 which comprises a first group of parallel elongate slots extending across the base portion 250 in a generally radial direction relative to the filter member 3 and which communicate with the drainage channels in the walls 251 and 252. The elongate members on the opposed side walls 253 and 254 are also integrally formed with the base portion 250 but form second and third groups of elongate slots extending orthogonally relative to the slots of the first group and which communicate, respectively, with the drainage channels in the walls 253 and 254.

In use of the tissue separation and collection device of FIGS. 1 to 9, the effluent stream is directed into the housing of the device in an upward direction of travel. At least a part of said effluent stream is deflected radially and downwardly into a filter receptacle 15 in which entrained tissue is retained in the filter receptacle and fluid passes through the elongate slots in the base portion 250 of the selected receptacle. The residual filtered fluid emerging through the slots is withdrawn in a downward direction through the outlet aperture 7a located below the filter receptacle 15, and removed via outlet port 7. The effluent stream is drawn through the device by a suction source applied to the outlet port 7.

The incoming fluid at inlet port 6 flows upwards through channel 21 and, with the relative positioning of the member 3 and lid member 1 shown in FIG. 5, the stream with entrained tissue travels through the through-hole 18 and is deflected radially above the member 3 and is drawn downwardly in the receptacle 15 located to the left in FIG. 5. Tissue is retained in the receptacle by the slotted basket 25 whilst fluid is drawn through the slots and downwardly through the associated channel 26 into the outlet port 7. The medical practitioner is able to confirm safe trapping of the sample through viewing window 4. In addition the slotted basket 25 is designed to allow escape of liquid effluent even when the receptacle is filled with solid effluent contaminant. The medical practitioner can then rotate the filter member 3 relative to the lid member 1 and base member 2 so as to align the fluid channel with the adjacent receptacle 15, which in turn becomes aligned with the outlet port 7. Should it become desired at any point, the operator may instead select a rotational position between baskets, which results in the bypass pathway being selected so that the fluid is deflected radially before passing up through the through-hole 18 and thus passes directly to the outlet without being filtered. In the embodiment shown the filter member is rotatable in a clockwise direction relative to the base member 2 and lid member 1, and is constrained by ratchet means (not shown) from counter rotation. In that way the filter member is only allowed to rotate in one direction so that after using the first filtration receptacle labelled 1 it is sequentially positioned with the receptacles 2, 3 and 4 in opposite the viewing member. It therefore cannot rotate in a counter direction from filtration receptacle, such as for example directly from "1" to filtration receptacle "4" which is adjacent to receptacle 1 in the counter-clockwise direction.

The viewing lens 4 advantageously has a calibrated grid over its surface (not shown in the drawings) to enable the medical practitioner to calculate the size of the biopsy material for later recording Once the collection sequence has been completed, the filter member 3 is removed from the base member 2, with the lid member 1 still in place on the top of the filter member 3, and the filter member and lid member are transferred together with the enclosed samples into a formalin pot which is closed and despatched for analysis without any need to disturb the collected samples.

In a second embodiment of the invention in which there is only one filter receptacle, the exterior of the device may be the same as or different from that of the first embodiment. In an illustrative device according to the second embodiment as shown in FIGS. 10 to 14, the exterior of the device is the same as the exterior of the illustrative device of the first embodiment as shown in FIGS. 1 to 3 and unless the contrary is indicated herein, where the same reference numerals are used in FIGS. 10 to 14 they have the same meaning as in FIGS. 1 to 9. However, the filter member 3 is in the form of a single basket forming single receptacle 150 having a multiplicity of slots, and a hollow tubular structure having a continuous circumferential wall 290 is provided in communication with the aperture 18. In the assembled device the other end of the wall 290 communicates with inlet port 6 via the inlet aperture 6a. In the device of FIGS. 10 to 14 the single basket 150 offers a large receptacle which may expediently be used to collect large volumes of tissue that might be encountered when performing a complex dissection of a large lesion that as divided up into multiple small parts as seen in endoscopic mucosal resection (EMR). The device of FIGS. 10 to 14 may, however, also be used for collecting a smaller amount of tissue, including a single sample of tissue, or a number of samples of tissue where it is deemed unnecessary for those samples to be individually collected in difference receptacles. The lid and base member may be rotatable together relative to the filter member 3 in order to enable the lens to be positioned over different parts of the basket. However, it is also possible if desired for the base member to co-rotate with the filter member in that embodiment since there are no separate baskets with respective filter pathways.

In a third embodiment of the invention, the device is a variant of the device shown in FIGS. 1 to 9. The device of the third embodiment is in most respects the same as that of the embodiment of FIGS. 1 to 9, but the separation member is modified to allow illumination of the collected tissue as will now be described. With reference to FIGS. 15 and 16, the separation member 300 of the third embodiment is provided with illumination windows 301, 302, 303 and 304 within the circumferential wall 312. The windows may if desired each be provided with a transparent membrane (not shown) to prevent contamination entering through the windows. At least in the regions in the vicinity of the receptacles 15, the circumferential wall 312 is arranged to permit transmission of light of desired wavelengths, for example it may be formed of a material that is transparent or translucent, allowing sufficient light to pass through to illuminate the interior of a receptacle including any collected sample(s) therein. A light filter insert 305 (see FIG. 16) has a collar 306 mountable about the lower annular portion of the centrally located structure 21 of the base member 2, which may otherwise be as shown in FIG. 3. Extending radially outwardly from the collar 306 are four spokes 307, 308, 309, 310, to each of which is attached a filter element 311, 312, 313, 314. When mounted within the device with the collar 306 about the central lower annular portion of structure 21 of the base member 2, the position of the filter elements 311, 312, 313 and 314 is fixed with reference to the separation member 300 by means of interlock pins 315, 316, which interlock with apertures 317, 318 in the separation member 300 (see FIG. 18). Each filter element 311, 312, 313 and 314 is then located between two adjacent filter receptacles 15, whilst the separation member 300 including the filter receptacles 15 and filter insert 305 are together rotatable relative to the base member 2. In use, in a first position the device is located with one of the receptacles 15 in register with a source of light and the light passes through the circumferential wall 312 resulting in diffuse illumination of the receptacle 15 and any sample therein. When the light is directed instead at one of the respective illumination windows 301, 302, 303, 304, light entering through those windows 301, 302, 303 and 304 and filtered by the aligned filter element 311, 312, 313 or 314 can enter the receptacles through the receptacle walls and any other adjacent structures. For example, in one suitable arrangement, internal structures including at least parts of the receptacle walls are arranged to transmit light of desired wavelengths, for example they may be translucent, allowing sufficient light to pass through to illuminate the interior of the receptacle including any collected sample(s). Since the light entering through the windows is filtered through one of the filter elements 311, 312, 313, 314 the resultant light is of a selected wavelength or range of wavelengths and is of a characteristic colour.

That light can pass through those parts of the internal structure that can transmit light and may thus enter the receptacles where the illuminated sample may be viewed through the magnifying lens 4. However, because of the selective filtering of the light, the light entering the receptacles when the illuminating windows are located between receptacles is essentially limited to the wavelengths selectively transmitted by the filter elements, with the result that the colour of the illuminating light reaching the receptacles is different from the colour that is transmitted into the receptacles 15 when the receptacles are aligned with an illumination source resulting in illumination of the receptacles through the wall 312 of the device. That can allow immediate recognition of the operational position of the device through the colour of illumination.

In one embodiment, a suitable illuminating device generates light principally in the visible spectrum, and the filter elements 311, 312, 313 and 314 are coloured filters, for example they may be selected to transmit preferentially red light. In those circumstances, red illumination of the receptacles 15 will be indicative of non-alignment of the illuminating windows and the receptacles which will further indicate that the filter member 3 is located between sample collection positions so that the effluent fluid is not being filtered in the device. Other suitable illumination wavelengths may be used, for example UV or IR. Endoscopic examinations are often carried out in a room having reduced lighting, and illumination of the receptacles as illustrated by the said third embodiment may be found advantageous in such low-lighting environments. For example, it may be considerably easier for the clinician to see when a tissue sample has been collected in the visible receptacle, so facilitating reliable separation of samples retrieved sequentially from different locations during the endoscopic examination.

FIG. 19 shows an illumination device which may be used with a tissue separation and collection device according to any of the embodiments described here. The illumination device together with a tissue separation and collection device preferably adapted for use therewith, may constitute a kit. In one embodiment, the illumination device together with a separation and collection device having a separation member 300 and filter as shown in FIGS. 15 to 18, may constitute a kit. The illumination device (torch) 400 comprises a housing 401 which is removably retained in a bracket 402. Where the illuminating device is battery-operated, the housing can contain one or more batteries. Light is emitted through torch lens 403, which is configured to emit a narrow beam of light. The housing 401 is attached to a mount 404, which has an upper surface 405 which is configured for cooperating engagement with the underside of the base member 2 of the tissue separation and collection device, whilst not interfering with the inlet or outlet paths to/from the separation and collection device. When the mount 404 is engaged with the collection device, the separation member 300 is rotatable with respect to the base member 2 of the device, the base member remaining stationary in mount 404. Rotational positioning of separation member 3 with the receptacles in register with the torch results in incident light entering the device through the circumferential wall 312, the light being transmitted through the wall into the basket to provide diffuse lighting of the basket and sample. If the separation member 300 is then rotated such that one of the lateral illumination windows 301, 302, 303, 304 is aligned with illumination device 400, light enters through the illumination window and is filtered by the aligned filter element, with the result that light transmitted through the internal structures into the receptacle 15 is of a colour determined by the filter element. Advantageously, the rotary movement of the separation member 300 is such that the separation member has a finite number of index positions corresponding to the number of windows, whereby the separation member preferably stops at a position in which the illumination window is aligned with the incident illumination from torch 400.

In other kit embodiments, the illumination device may be used with other tissue separation and collection devices, for example as shown in FIGS. 1 to 10, or FIGS. 10 to 14, or FIGS. 22 to 30 or FIGS. 31 to 33. With those device, the illumination device may usefully provide illumination within the device by means of transmission of light through the exterior of the device. When used with an illumination device it may be expedient to form the tissue separation and collection device, or at least a part thereof through which light is desired to be transmitted, to be formed of a material that transmits light. Advantageously, the material will be translucent, permitting diffuse lighting of the desired parts of the interior of the device.

FIG. 20 shows the illumination device of FIG. 19, additionally indicating by broken lines a device 1 having illumination windows, for example a device of the third embodiment described above. In use, the narrow beam of light generated by the illumination device 400 via lens 403 enters the collection device with minimal stray light that may cause distraction to operating theatre staff. The illumination generated in the device is dependent on whether the device is in the "use" position (for sample collection) or not as described above.

The illumination windows serve in part to distinguish clearly between positions in which samples will be collected and positions in which fluid will pass through the device without filtering. It will be appreciated that kits of the invention include separation devices in which the above-described illumination windows are absent and in which the illumination is used for simple illumination of samples by transmission through the external walls of the device.

With reference to FIG. 21, there is shown an embodiment of the device of the invention which includes a data storage element 500 in the form of a QR code. The QR code enables information unique to the patient and the harvested samples to be collected and reliable stored electronically for future use in other remote departments which are able to access the information store. Whilst shown in FIG. 20 with reference to a device according to FIGS. 1 to 9 it will be appreciated that machine readable elements of any suitable kind may be used in any of the embodiments described.

In a further embodiment shown in FIGS. 22 to 29, a device for separation and collection of tissue has a housing 600, formed by three cooperating portions comprising lid member 601, base member 602 and separation member 603. Lid member 601 is of generally similar construction to the lid member 1 of the first embodiment, includes a generally planar circular upper wall with a bevelled lateral portion which together form an upper wall 601a of the device, and from which depends an annular flange 610. Base member 602 includes a generally planar circular wall forming lower wall 602a of the device and from the periphery of which extends upwardly an annular flange 619. An upwardly extending hollow cylindrical structure 621 is located in a central region of the base member 602 to define pathway 628 providing fluid communication between the inlet port 6 and the interior of the housing 600. The base member 602 has a centrally located inlet comprising an inlet aperture 606a which is connectable to an upstream suction line 653 by an inlet port 606 through which, in use, effluent from a scoping device is delivered to the inlet aperture 606a, and an eccentrically located outlet aperture 607a that is connectable to a downstream suction line (not shown) by exit port 607 through which the filtered fluid is, in use, discharged under suction applied to exit port 607. Separation member 603 includes a circumferential wall 612 which, in the assembled device, extends between the upper wall 601a and lower wall 602a and forms a lateral enclosing wall of housing 600. The separation member 603 further includes a filter member 603a which is mounted within the circumferential wall 612 and, in the embodiment of FIGS. 22 to 29 Is integrally formed with the said wall. The housing 600 thus encloses filter member 603a vertically between said upper wall 601a, and said lower wall 602a and laterally enclosed by wall 612. The filter member 603a has four filter receptacles 615. The upper wall 601a comprises a viewing window 604 for viewing tissue collected in the filter member 603a. The viewing window 604 comprises a generally circular lens. A measurement scale (not shown in the drawings) may be provided in association with the viewing window, for enabling determination of size of a sample viewed through the viewing window. A suitable measurement scale may be incorporated into the viewing window, for example as a calibration grid within the window or on a surface thereof. A projection 615 serves to reduce stray light that may otherwise reach the viewing window 604. The projections 5, 605 may additionally serve as an injection point where the lid member 1 is made by injection moulding.

In the embodiment of FIGS. 22 to 29, the upper wall 601a may be of polished plastic in order that it is transparent allowing good visibility of collected samples received in the filter receptacles 615. The filter receptacles 615 are so configured and dimensioned that they preferentially retain solid material in a location that in use will be substantially alignable with a central portion of the viewing window 604, for example a location arranged centrally within the receptacle. The or each filter receptacle has an upper rim 652 defining an upper opening in an upper surface of the filter member 603a and, in the assembled device, opposed to said upper wall 601a. A lower filtration region of each receptacle 615 comprises a fluid-permeable floor 650 defining a plurality of elongate apertures 651a for allowing passage of the fluid. Additional elongate apertures 651b are provided in side walls 653 of the receptacles 615.

The inlet aperture 606a is located centrally beneath the filter member 603a in the lower wall 602a. The outlet aperture 607a is located eccentrically in the lower wall 602a, and is locatable sequentially under each receptacle by rotation of the base member and lid member relative to the filter member 603a. Multiple parallel ridges 654 are provided on the wall 612 to improve grip when an operator rotates the separation member 603 relative to the lid and base members 601, 602. The device 600 comprises a fluid pathway 628, generally indicated by arrows in FIG. 26, for delivering effluent stream received through the inlet aperture 606a upwards through filter member 603a, diversion into the selected filter receptacle 615 and delivery of filtered fluid exiting through the elongate apertures 651a, 651b of the receptacle 615 to outlet aperture 607a.

The fluid pathway 628 is in most respects similarly formed to the fluid pathway 28 of the device of FIGS. 1 to 9. The pathway extends upwardly axially through a central aperture 655 in the filter member 603a where a fluid directing member 656 provided on the inner surface of upper wall 601a has a depending wall 657 which defines an opening 658 through which fluid is selectively directed radially outwards via a cooperating channel-shaped inlet 659 formed in the wall of the selected receptacle 615 that is located in register with the outlet port 607 and into that selected receptacle. A locking mechanism for locking lid member 601 and base member 602 to avoid separate rotation of those portions is provided and in most respects is of similar structure to that of the embodiment of FIGS. 1 to 9. In contrast to the embodiments of FIGS. 1 to 9, however, two projections 622a, 622b are shorter than the projections 22a, 22b and do not extend fully through the upper wall 601a, but are instead received in recesses formed in or near the upper wall which serve to lock the base member 602 and lid member 601 in a common rotational position and prevent separate rotation of one of the said portions during tissue collection.

When viewing window 604 is not in register with a receptacle but is rather located between receptacles, a bypass pathway is formed beneath the filter member 603a so that the effluent passes directly from the cylindrical structure 21 into the void region beneath the receptacles 615 without passing through the filter receptacles. The effluent is able to pass between projections 609a, 609b, 622a, 622b via the void areas defined between the curved curtain members 629 (which are of similar structure to curtain members 29), the curtain members 629 being positioned generally in register with the respective projections so as to leave an unobstructed pathway between the curtain members 629 for passage of bypass flow when the lid member 601 is so rotated that it is positioned between receptacles.

A protrusion 660 is provided on lid member 601 at the periphery of the upper wall adjacent to viewing window 604, and serves with tab 661 on base member 602 to provide a visible and/or tactile indication of correct relative positioning of the lid member and base member. The tactile indication of correct positioning is in particular useful where surrounding light levels are low.

The filter member 603a is mounted within the circumferential wall 612, and the base member 602 comprising said lower wall 602a and lid member 601 comprising said upper wall 601a are each removably attached to the circumferential wall 612 in such a manner that they form a seal in use at least when suction is applied to the device. The seal between the lid member 601 and separation member 603 is provided by means of a circumferential ridge 662 protruding from the outer surface of depending annular flange 610 of device 600. In the assembled device the ridge 662 is able to provide circumferential sealing contact with the inner surface of circumferential wall 612 at or near an enlarged upper rim 663 of wall 612. Analogously, circumferential ridge 664 on the outer surface of annular flange 619 of base member 602 provides circumferential sealing contact with separation member 603 at or near an enlarged lower rim 665 of wall 12. At least in use the housing 600 of the devices of the embodiments is substantially sealed with the exception of said inlet aperture and said outlet aperture, at least when a vacuum is applied to outlet port 7, 607.

As can be seen from FIGS. 25 and 26, the receptacles 615 are deeper than the receptacles 15 of the embodiment of FIGS. 1 to 9, the rims 651b surrounding the mouths of the receptacles 615 being close to or in contact with the undersurface of upper wall 602a. It has been found that the provision of the higher side walls 653 is advantageous in reducing undesirable splashing of effluent into an adjacent receptacle. Thus, the elongate apertures 651b are able to extend from the floor of the receptacles 615 up towards the rim of the receptacle. Device 600 also differs from the embodiment of FIGS. 1 to 9 in that the channels 26 are absent. The absence of channels 26 can give enhanced fluid drainage, allowing a larger area of the receptacle to be provided with drainage apertures 651b, as is most easily discernible from FIG. 25.

Also present is an indexing and latching mechanism which serves preferentially to position the base member 602 and lid member in a selected rotational position relative to the separation member, such as a selected filtering position or a selected non-filtering position. A detent 666 provided on the inner surface of the lower wall 602a in the vicinity of the inlet aperture 606a is positioned to interact with a radial extension 667 on the separation member to prevent rotation of the receptacles in the wrong (reverse) direction, thereby preventing subsequent samples being delivered into a receptacle that has already been used to collect a sample.

The material from which the housing is formed is preferably selected such that at least a portion of the circumferential wall is able to transmit light from an external source into the device for illumination of a said at least one filter receptacle. In the housing 600 arrows 668 are printed onto the exterior of wall 612. The arrows are printed in a different colour from the surrounding wall and are of a colour that makes them easily visible, for example glow, when light impinges on them. They are configured to indicate the direction of rotation of the device and so positioned circumferentially that illumination of an arrow serves as a warning of alignment of the receptacles with the non-collecting position in which fluid bypasses the receptacles 615 without collection of entrained tissue. In order to improve illumination within the receptacles 615 through the housing, a peripheral portion of the filter member 603a is absent radially outside the receptacle wall 653 forming a void region 669 through which light entering through wall 612 can reach a portion of wall 653 with reduced interruption by solid material of the filter member.

Raised elements 670 are provided on lower wall 602a to serve as locating means for mounting the device in a support with cooperating recessed regions, for example forming a friction fit. The elements 670 in the embodiment are configured and dimensioned for engaging in the correspondingly configured and dimensioned recesses in the mount 404 of the illumination device of FIGS. 19 and 20.

The device of FIGS. 22 to 29 is usable in generally analogous manner to that of FIGS. 1 to 10.

Whilst the filter member 603 has four receptacles, it may instead have a different number, for example from three to five, filter receptacles.

Device 700 is in many respects the same as the device of FIGS. 22 to 27, and in particular the lid member and base member are the same. In the device 700 the separation member 703 has a filter member 703a with a single filter receptacle 715. The filter receptacle 715 is relatively deeper than the single receptacle 150 of the device of FIGS. 10 to 14, and has a rim 701 which in the assembled device sits in contact with or close to the inner surface of upper wall 601a. The filter receptacle 715 comprises a flattened floor 702. Two continuous annular ribs 703, 704 of plastic are integrally formed with the floor of the filter receptacle and serve to add strength, particularly during relative movement of parts, thus reducing any tendency to distortion. The receptacle has slots 705 of width similar to the elongate slots of the embodiment of FIGS. 10 to 14 but are divided longitudinally by the annular ribs 703, 704 into three elongate portions 705, 706, 707, as may best be seen from FIG. 32. As compared with the embodiment of FIGS. 10 to 14, the deeper receptacle 715 can provide increased ease of filtering and/or easier removal of fluid. Further, the fact that the upper rim 701 of filter member 703 is in use close to or in contact with the lower surface of the upper wall 603a further enhances the efficiency with which the fluid is in use directed into the filter receptacle 715. The separation member 703 has a centrally located cylindrical tube 708 which, in the assembled device, communicates at its lower end with inlet aperture 606 of the base member and at its upper end with a central aperture 709. On emerging from central aperture 709, effluent is diverted radially into the filter receptacle 715 where entrained tissue is retained and fluid passes through the elongate apertures and is withdrawn through the outlet aperture 707a. A fluid pathway 710 is thus formed extending from inlet aperture 606a via tube 708 and receptacle 715 to the outlet aperture 707a. A fluid bypass pathway is not provided in the embodiment of FIGS. 31 to 33, where the volume of the filter receptacle 715 is more easily able to accommodate larger flows of fluid even when the receptacle contains some collected tissue.

The separation member 703 engages with lid member 601 and base member 612 in analogous fashion to separation member 603, to form a seal between the inner surface of circumferential wall 712 and the respective circumferential ridges 662 and 664 on flanges 610 and 619, thereby serving to form a seal when suction is applied to the outlet port 607.

The devices described above may in practice be used with tubing attached to the inlet port and outlet port. In particular, in some embodiments a relatively long flexible tubing, for example 300 to 600 mm tubing, such as silicone tubing, may expediently be attached to the inlet port 7, 607 of the device. In other embodiments, a shorter tube may be used, for example in some embodiments there may be used polymer tubing of length less than 300 mm, for example 50 mm to 250 mm. In some embodiments a less flexible tubing may be desirable, allowing the device to be effectively supported by the tubing. For example, a PVC tubing may expediently be used in those embodiments.

The location of the inlet and outlet ports away from the top surface, especially in the base of the device, enables size to be reduced without loss of visibility of collected samples. It is also an advantage that tubing attached to the inlet and outlet ports is removed from the top of the device, so that it does not interrupt the medical operative's view of the viewing window. Further, through the efficient design it is possible to make the device of a size sufficiently small that the filter member and lid member can be detached from the base member and, still as a closed unit, placed in a formalin pot of the size (20 ml) typically used for biopsy samples, thereby reducing the risk of exposure of staff to infection or to toxic materials. In the case of collection of multiple samples that enables any errors in transcription of information relating to multiple samples through inadvertent switching of samples when they are removed from a polyp trap device for transfer to a receptacle for sending for pathological examination.

Illustrative embodiments of the invention described herein with reference to the drawings are of generally circular circumference, having a circumferential wall which is annular. It is not essential that the devices of the invention are of circular circumference. For example, they may be of polygonal circumference, such as rectangular (including square rectangular), pentagonal, heptagonal or octagonal defined by a correspondingly configured circumferential wall. Where the device has a polygonal circumference, it will be preferable for the number of polygon sides to correspond to the number of filter receptacles, with each polygon side preferably forming an outer boundary of a respective filter receptacle.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A device for separation and collection of tissue from an effluent stream of tissue and carrier fluid generated in a medical procedure, the device comprising a housing having an upper wall, a lower wall, a circumferential wall extending between the upper wall and lower wall, an inlet aperture for receiving the effluent stream and an outlet aperture for discharge of filtered fluid, wherein the housing encloses a filter member positioned between said upper wall and said lower wall and comprising at least one filter receptacle, said at least one filter receptacle comprises a recess having an upper opening in an upper surface of the filter member and opposed to said upper wall, communicating with a lower filtration region having a fluid-permeable floor comprising a plurality of apertures for allowing passage of the fluid, the upper wall comprises a viewing window for viewing tissue collected in the filter member, the inlet aperture is located beneath the filter member, and the device comprises a fluid pathway for delivering effluent stream received through the inlet aperture into a said filter receptacle from above the filter member.

2. A device according to claim 1, wherein the inlet aperture and the outlet aperture are located in the lower wall.

3. A device according to claim 1, wherein the viewing window is movable relative to the filter member.

4. A device according to claim 1, wherein said at least one filter receptacle is so configured and dimensioned that it preferentially retains solid material in a location that in use will be substantially alignable with a central portion of the viewing window.

5. A device according to claim 2, wherein the inlet aperture is centrally located within the lower wall and the fluid pathway comprises a through-hole in the filter member, the inlet aperture and the through-hole forming an axially extending pathway communicating between the inlet aperture and upwardly through the filter member.

6. A device according to claim 1, wherein the filter member is mounted within the circumferential wall, and a base member comprising said lower wall and a lid member comprising said upper wall are each removably attached to the circumferential wall.

7. A device according to claim 6, wherein the lid member is attached to the base member, and the lid and base members are rotatable together relative to the filter member.

8. A device according to claim 7, further comprising an indexing and latch mechanism which serves preferentially to position the lower wall selectively in one of a number of filtering positions or in one of a number of positions in which filtering is circumvented.

9. A device according to claim 1 having an overall diameter of from 2.5 to 5 cm.

10. A device according to claim 1, further comprising indicia identifying at least one receptacle.

11. A device according to claim 1, wherein the viewing window comprises a magnifying lens.

12. A device according to claim 1, further comprising a measurement scale for enabling determination of size of a sample viewed through the viewing window.

13. A device according to claim 1 wherein at least a portion of the circumferential wall is able to transmit light from an external source into the device for illumination of a said at least one filter receptacle.

14. A device for separation and collection of tissue from an effluent stream of tissue and carrier fluid generated in a medical procedure, the device comprising a housing having an upper wall, a lower wall, a circumferential wall extending between the upper wall and lower wall, an inlet aperture for receiving the effluent stream and an outlet aperture for discharge of filtered fluid, wherein the housing encloses a filter member positioned between said upper wall and said lower wall and comprising at least one filter receptacle, the upper wall comprises a viewing window for viewing tissue collected in the filter member, the inlet aperture is located beneath the filter member, and the device comprises a fluid pathway for delivering effluent stream received through the inlet aperture into a said filter receptacle from above the filter member wherein:
(a) the inlet aperture and outlet aperture are located in said lower wall of the device;
(b) the filter member is optionally rotatable relative to the viewing window for enabling a tissue sample collected in a said filter receptacle to be located in register with the viewing window, wherein the rotation is permitted only in one direction;

(c) said at least one filter receptacle comprises a fluid-permeable base portion which can comprise a plurality of elongate apertures; and (d) said at least one filter receptacle is so configured that in use any collected tissue tends to be collected and retained in a region of the filter receptacle that is alignable with a central region of the viewing window.

15. A device according to claim 1, wherein the filter member comprises a plurality of filter receptacles, and the filter member and the outlet aperture are rotatable relative to one another, whereby the outlet aperture may be aligned with a selected filter receptacle.

16. A device according to claim 1, wherein the filter member is so rotatable that the effluent stream can be directed to a selected filter receptacle.

17. A device according to claim 1, wherein the filter member comprises a single filter receptacle.

18. A kit comprising a tissue separation and the device according to claim 1 and an illumination device for providing illumination to a said circumferential wall for illumination of at least a part of the device and/or for illumination of a said filter receptacle therein.

19. A kit according to claim 18, further comprising at least one mounting member for so mounting the illumination device and the tissue separation and collection device relative to one another that the illumination device, in use, directs incident light towards said circumferential wall or a lateral illumination window therein.

20. A kit according to claim 18, wherein the tissue collection device has two or more tissue retention locations, and the tissue retention locations are movable relative to the illumination device to enable one or more tissue retention locations to be selectively illuminated.

21. A method of separating tissue from an effluent stream in which tissue is entrained in a carrier fluid, comprising directing the effluent stream into a housing of a tissue separation and collection device in an upward direction of travel, the tissue separation and collection device comprising the housing, the housing having an upper wall, a lower wall, a circumferential wall extending between the upper wall and lower wall, an inlet aperture for receiving the effluent stream and an outlet aperture for discharge of filtered fluid, wherein the housing encloses a filter member positioned between said upper wall and said lower wall and comprising at least one filter receptacle, said at least one filter receptacle comprises a recess having an upper opening in an upper surface of the filter member and opposed to said upper wall, communicating with a lower filtration region having a fluid-permeable floor comprising a plurality of apertures for allowing passage of the fluid, the upper wall comprises a viewing window for viewing tissue collected in the filter member, the inlet aperture is located beneath the filter member; deflecting at least a part of said effluent stream downwardly into said at least one filter receptacle in which entrained tissue is retained in the filter receptacle and fluid passes through the receptacle, and withdrawing the filtered fluid in a downward direction through said outlet aperture located below the filter receptacle.

22. A method according to claim 21, wherein the effluent stream is drawn through the device by means of suction applied to the outlet aperture.

23. A method according to claim 21, wherein the effluent stream is optionally intermittently deflected from said upward direction of travel into a bypass pathway from which it is withdrawn through the outlet aperture without passing through a said filter receptacle.

24. A method according to claim 23, wherein said deflection is effected by means of relative rotation of a first part of the housing relative to a second part of the housing.

25. A method of preparing a tissue sample for pathological analysis, comprising collecting the tissue in a device according to claim 1, and placing the filter member containing the tissue into formalin in a receptacle.

26. A method according to claim 25, wherein the filter member is accompanied by a lid member of the device, whereby the tissue sample or samples is/are enclosed.

27. A method for collecting and analysing a tissue sample, wherein the tissue sample is collected in accordance with a method according to claim 21, the filter receptacle and collected sample therein are immersed in preservative fluid, such that air in the filter receptacle is expelled and the collected sample is submerged in preservative fluid, delivering the immersed filter receptacle to an analysis location, wherein the collected sample is retained within the filter receptacle at least until it reaches the analysis location.

28. A method according to claim 27, wherein the sample is enclosed within the filter receptacle by closure means at least until it reaches the analysis location.

29. A method according to claim 28, wherein multiple samples are collected in a device having a multiplicity of filter receptacles and the closure means serves to close each filter receptacle such that transfer of enclosed collected tissue from one filter receptacle to another is prevented.

30. A device for separation and collection of tissue from an effluent stream of tissue and carrier fluid generated in a medical procedure, the device comprising a housing having an upper wall, a lower wall, a circumferential wall extending between the upper wall and lower wall, an inlet aperture for receiving the effluent stream and an outlet aperture for discharge of filtered fluid, wherein the housing encloses a filter member positioned between said upper wall and said lower wall and comprising at least one filter receptacle, the upper wall comprises a viewing window for viewing tissue collected in the filter member, the viewing window is movable relative to the filter member, the inlet aperture is located beneath the filter member, and the device comprises a fluid pathway for delivering effluent stream received through the inlet aperture into a said filter receptacle from above the filter member.

* * * * *

UNITED STATES PATENT AND TRADEMARK OFFICE
CERTIFICATE OF CORRECTION

Page 1 of 1

PATENT NO. : 10,835,650 B2
APPLICATION NO. : 15/764486
DATED : November 17, 2020
INVENTOR(S) : Patrick Axon It is certified that error appears in the above-identified patent and that said Letters Patent is hereby corrected as shown below:

On the Title Page

Item (30) Foreign Application Priority Data:
"Oct. 9, 2015 (GB) ............................1517921.1"
Should read:
-- Oct. 9, 2015 (GB) ............................1517921.1
May 20, 2016 (GB) ............................1608964.1 --

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*